(12) United States Patent
Berndt et al.

(10) Patent No.: US 11,306,089 B2
(45) Date of Patent: Apr. 19, 2022

(54) GAMMA-CARBOLINE COMPOUNDS FOR THE DETECTION OF TAU AGGREGATES

(71) Applicants: AC IMMUNE SA, Lausanne (CH); LIFE MOLECULAR IMAGING SA, Matran (CH)

(72) Inventors: Mathias Berndt, Berlin (DE); Andre Müller, Berlin (DE); Felix Oden, Berlin (DE); Hanno Schieferstein, Wiesbaden (DE); Heribert Schmitt-Willich, Berlin (DE); Heiko Kroth, Ecublens (CH); Jérôme Molette, Prevessin Moens (FR)

(73) Assignee: LIFE MOLECULAR IMAGING LIMITED, Warwick (GB)

( * ) Notice: Subject to any disclaimer, the term of this patent is extended or adjusted under 35 U.S.C. 154(b) by 0 days.

(21) Appl. No.: 16/964,952

(22) PCT Filed: Jan. 22, 2019

(86) PCT No.: PCT/EP2019/051495
§ 371 (c)(1),
(2) Date: Jul. 24, 2020

(87) PCT Pub. No.: WO2019/145291
PCT Pub. Date: Aug. 1, 2019

(65) Prior Publication Data
US 2021/0047321 A1    Feb. 18, 2021

(30) Foreign Application Priority Data
Jan. 24, 2018  (EP) ..................................... 18153325

(51) Int. Cl.
| A61K 51/00 | (2006.01) |
| A61M 36/14 | (2006.01) |
| C07D 471/04 | (2006.01) |
| A61K 51/04 | (2006.01) |
| C07B 59/00 | (2006.01) |
| C07D 513/14 | (2006.01) |

(52) U.S. Cl.
CPC ........ C07D 471/04 (2013.01); A61K 51/0455 (2013.01); C07B 59/002 (2013.01); C07D 513/14 (2013.01); C07B 2200/05 (2013.01)

(58) Field of Classification Search
CPC .............. C07D 471/04; C07D 513/14; A61K 51/0455; C07B 59/002; C07B 2200/05
USPC ........................................................ 424/1.89
See application file for complete search history.

(56) References Cited

FOREIGN PATENT DOCUMENTS

| WO | 2013176698 A1 | 11/2013 | |
| WO | WO-2015110263 A1 * | 7/2015 | ......... A61K 51/0455 |
| WO | 2016124508 A1 | 8/2016 | |
| WO | WO-2018015549 A1 * | 1/2018 | .............. A61P 27/06 |
| WO | WO-2018024642 A1 * | 2/2018 | ........... C07B 59/002 |

OTHER PUBLICATIONS

"International Search Report and Written Opinion for PCT/EP2019/051495", issued by the European Patent Office (EPO) as international searching authority dated Feb. 27, 2019.
Xia, et al., "[18F]T807, a novel tau positron emission tomography imaging agent for Alzheimer's disease", Alzheimer's & Dementia: The Journal of the Alzheimer's Association, vol. 9, No. 6, Oct. 1, 2013, pp. 666-676.

* cited by examiner

*Primary Examiner* — Michael G. Hartley
*Assistant Examiner* — Sean R Donohue
(74) *Attorney, Agent, or Firm* — Millen White Zelano & Branigan, PC

(57) ABSTRACT

The present invention relates to novel compounds of the formula (II) and formula (III)

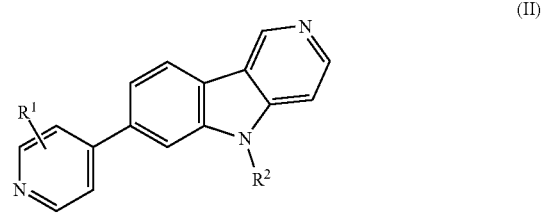

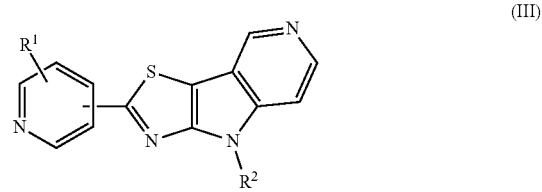

that can be employed in the selective Tau detection of disorders and abnormalities associated with Tau aggregates such as Alzheimer's disease and other tauopathies using Positron Emission Tomography (PET) Imaging.

31 Claims, No Drawings

GAMMA-CARBOLINE COMPOUNDS FOR THE DETECTION OF TAU AGGREGATES

CROSS-REFERENCE TO RELATED APPLICATIONS

This application is a National Stage application of International Application No. PCT/EP2019/051495, filed Jan. 22, 2019 which claims priority to European Application 18153325.8, filed on Jan. 24, 2018. The entire contents of the above-identified applications are hereby fully incorporated herein by reference.

FIELD OF INVENTION

The present invention relates to novel compounds of the formula (II) and formula (III) that can be employed in the selective detection of disorders and abnormalities associated with Tau aggregates such as Alzheimer's disease (AD) and other tauopathies, for example, using Positron Emission Tomography (PET) imaging. The present invention also refers to intermediates which can be used in the production of such imaging compounds. Diagnostic compositions as well as methods of imaging or diagnosing using the above compounds and kits which are useful for preparing a radiopharmaceutical preparation are also subject of the present invention.

BACKGROUND

Alzheimer's disease is a neurological disorder primarily thought to be caused by amyloid plaques, an extracellular accumulation of abnormal deposit of amyloid-beta (Aβ) aggregates in the brain or in the eyes. The other major neuropathological hallmarks in AD are the intracellular neurofibrillary tangles (NFT) that originate by the aggregation of the hyperphosphorylated Tau (Tubulin associated unit) protein, phosphorylated Tau or pathological Tau and its conformers. AD shares this pathology with many neurodegenerative tauopathies, in particularly with specified types of frontotemporal dementia (FTD). In AD brain, Tau pathology (tauopathy) develops later than amyloid pathology, but it is still discussed controversially if Aβ protein is the causative agent in AD which constitutes the essence of the so-called amyloid cascade hypothesis (Hardy et al., Science 1992, 256, 184-185, and most recently, Musiek et al., Nature Neurosciences 2015, 18(6), 800-806, "Three dimensions of the amyloid hypothesis: time, space and 'wingmen'").

Presently, the only definite way to diagnose AD is to identify plaques and tangles in brain tissue by histological analysis of biopsy or autopsy materials after the death of the individual. Beside AD, Tau plays an important role in other (non-AD) neurodegenerative diseases. Such non-AD tauopathies include, for example, supranuclear palsy (PSP), Pick's disease (PiD) and corticobasal degeneration (CBD).

Therefore, there is a great deal of interest in detection of Tau pathology in vivo. Tau PET imaging promises novel insights into deposition of Tau aggregates in the human brain and might allow to non-invasively examine the degree of Tau pathology, quantify changes in Tau deposition over time, assess its correlation with cognition and analyze the efficacy of an anti-Tau therapy. For recent reviews see Shah et al., J Nucl Med. 2014, 55(6), 871-874: "Molecular Imaging Insights into Neurodegeneration: Focus on Tau PET Radiotracers", Jovalekic et al., EJNMMI Radiopharmacy and Chemistry 2016, 1:11, "New protein deposition tracers in the pipeline", and Ariza et al., J Med Chem 2015, 58(11), 4365-82: "Tau PET Imaging: Past, Present and Future". In addition, several patent applications have recently been published, e.g: WO 2013/176698, WO 2009/102498, WO 2011/119565, U.S. Pat. No. 8,932,557 B2 and U.S. Pat. No. 8,691,187,B2 (Siemens Medical Solutions, Lilly), WO 2012/067863 and WO 2012/068072 (both GE Healthcare) WO 2014/026881, WO 2014/177458, WO 2014/187762, WO 2015/044095, WO 2015/052105, WO 2015/173225 (Hoffmann-La Roche AG), WO 2015/188368 (Merck Sharp & Dohme) and WO 2016/124508 (UCB Biopharma SPRL) which claim novel compounds for Tau imaging.

In order to achieve high target selectivity, molecular probes have been used which recognize and bind to the pathological target. Selectivity for binding to pathological Tau protein over other protein depositions in the brain is therefore a basic requirement of a Tau imaging probe. In order to reduce background signal interference resulting from non-specific off-target binding (e.g. binding to Aβ or monoamine oxidases), imaging compounds should bind with high affinity to pathological Tau. Since amyloid or amyloid-like deposits formed from proteins of diverse primary amino acid sequences share a common β-sheet quaternary conformation, molecular probes are required that can differentiate such structures in order to avoid detection of other pathologies (false-positives) and therefore misdiagnosis.

Off-target binding to monoamine oxidase A or B have been reported to be a significant limitation for Tau tracers, especially T-807 and THK-5351 (Vermeiren, C, et al. Alzheimer's & Dementia. 2015; 11 (7) Supplement p1-2: "T807, a reported selective tau tracer, binds with nanomolar affinity to monoamine oxidase A"; Ng, K P, et al. Alzheimer's Research and Therapy 2017, 9:25: "Monoamine oxidase B inhibitor, selegiline, reduces $^{18}$F-THK5351 uptake in the human brain"). Off-target binding to monoamine oxidases A or B confound the interpretation of PET images with T807 and THK5351 with respect to tau. Presence of monoamine oxidases within several brain regions limits the interpretation of PET imaging results with these tracers.

Beside high selectivity, also binding to different Tau isoforms is an important aspect for a tau tracer. Up till now, most tracers show binding to tau in AD. However, tau in AD is a mixture of two isoforms, so called 3R-tau and 4R-tau. Other non-AD tauopathies are characterized by the predominant presence of one of these isoforms. In Pick's disease (PiD), the 3R tau isoform is predominantly present whereas in progressive supranuclear palsy (PSP) and in corticobasal degeneration (CBD), the 4R-tau isoform is the existing pathology.

In addition, molecular probes must also be designed such that upon administration they can distribute within the body and reach their target. For imaging of Tau aggregates associated with neurological disorders such as e.g. Alzheimer's disease, imaging compounds are required that can penetrate the blood brain barrier and pass into the relevant regions of the brain. For targeting intracellular Tau aggregates, cell permeability is an additional requirement of imaging compounds. A further prerequisite in order to get a sufficient signal-to-noise ratio is a fast compound wash-out from non-target regions in the brain (or other targeting organ). Also, compounds should show no defluorination, as bone uptake in the skull (as result from presence of free fluoride) will cause significant spill-over into the brain which limits the usability (Chien D T, et al. J Alzheimers Dis. 2014; 38:171-84).

The specifically disclosed and most advanced derivative of WO 2013/176698 is the 6-fluoropyridin-3-yl-pyridoindole [18]F-1 (also see U.S. Pat. No. 8,932,557 B2).

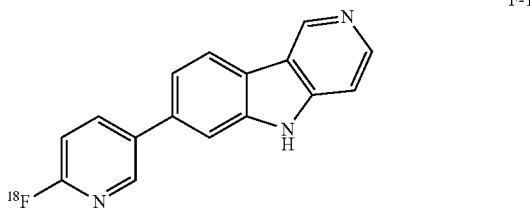

[18]F-1

Compound [18]F-1 was investigated in various clinical studies. Although [18]F-1 seems to be able to detect Tau in patients with AD or amyloid-beta positive mild cognitive impairment (MCI), various limitations have been reported.

Vermeiren and coworkers found that compound [18]F-1 bound to Monoamine oxidase A (MAO A) with a $K_D$ of 1.5 nM. Their data unanimously demonstrate that compound [18]F-1 binds to Tau aggregates and MAO-A with similar high affinity. The findings raise caution to the interpretation of compound [18]F-1 clinical data, as MAO-A is widely expressed in most human brain regions (Vermeiren et al., Alzheimers & Dementia. 2015; 11 (7) Supplement p1-2: T807—a reported selective Tau tracer, binds with nanomolar affinity to Monoamine oxidase A).

Compound [18]F-1 was reported to have a fairly strong signal in parts of the brain's basal ganglia, e.g., the striatum and substantia nigra, regardless of the patient's diagnosis. The signal of [18]F-1 in the cortex did not reach a "steady state" (a window of time during which the ratio of binding in a target region to binding in the reference tissue (i.e. cerebellum) was stable). In addition, the kinetics of [18]F-1 in various brain regions was different and never stabilized in a 150-minute scanning period (S. Baker, Human Amyloid Imaging Meeting, 2015).

Binding of compound [18]F-1 to AD brain sections was demonstrated by autoradiography. However, compound [18]F-1 showed limitations in binding to brain sections with pathologies of non-AD tauopathies: a) Lowe V J, et al. An autoradiographic evaluation of AV-1451 Tau PET in dementia. *Acta Neuropathologica Communications.* 2016; 4:58; b) Marquie M, et al. Validating novel Tau Positron Emission Tomography Tracer [F-18]-AV-1451 (T807) on postmortem Brain Tissue. *Annals of Neurology.* 2015; 78:787; c) Gomez F, et al. Quantitative assessment of [$^{18}$F]AV-1451 distribution in AD, PSP and PiD Post-Mortem Brain Tissue Sections relative to that of the anti-Tau antibody ATB. *Journal of Nuclear Medicine.* 2016; 57, S2: 348, d) Sander K, et al. Characterization of tau positron emission tomography tracer AV1451 binding to postmortem tissue in Alzheimer's disease, primary tauopathies, and other dementias. *Alzheimers Dementia* 2016, 12(11): 116-1124 e) Smith R, et al. Increased basal ganglia binding of 18F-AV-1451 in patients with progressive supranuclear palsy. *Movement disorders* 2016.

Also clinically, [18]F-1 seems to be of limited value for the detection of tau in PSP subjects: a) Smith R et al., Tau neuropathology correlates with FDG-PET, but nor with AV-1451-PET, in progressive supranuclear palsy. Acta Neuropathologica 2017, 133:149-151; b) Smith R, et al. Increased basal ganglia binding of 18F-AV-1451 in patients with progressive supranuclear palsy. *Movement disorders* 2017, 32(1), 108-114.

The final conclusions from these studies indicate that T807/AV1451 might not reliable to distinguish individual patients with PSP from controls. This is mainly attributed to an increased unspecific binding in midbrain structures like basal ganglia. Uptake seen in cerebral cortex and white matter did not reflected tau pathology in PSP.

In view of the above-mentioned prior art, it was an object of the present invention to provide a compound which has a high affinity and selectivity for Tau and is thus suitable as a PET imaging agent. Preferably, the compounds of the present invention demonstrate high affinity to Tau aggregates, high selectivity towards pathological Tau compared to other targets in the brain and favorable pharmacokinetic properties without defluorination.

SUMMARY OF THE INVENTION

Therefore, the present invention relates to the following items:
1. A compound of the formula (II)

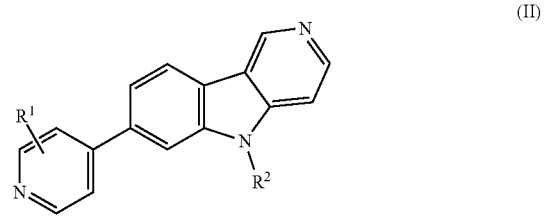

(II)

as well as pharmaceutically acceptable salts, hydrates, solvates, prodrugs and polymorphs thereof;
wherein
$R^1$ is selected from the group consisting of $^{18}$F, F and LG;
$R^2$ is H or PG;
PG is a protecting group;
LG is a leaving group,
wherein the hydrogen in the formula II are independently selected from $^1$H, $^2$H or [3]H.

2. The compound according to item 1, which is

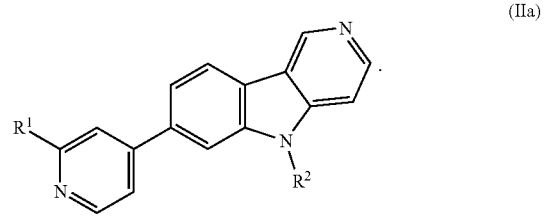

(IIa)

3. The compound according to item 1, which is

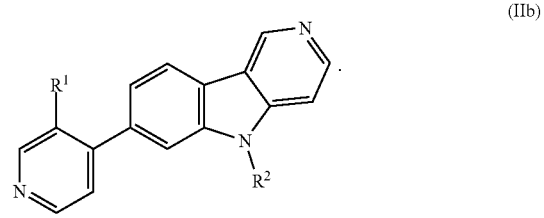

(IIb)

4. A compound of the formula (III)

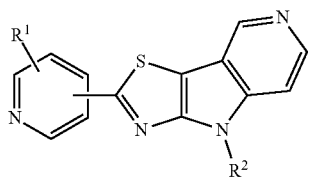

as well as pharmaceutically acceptable salts, hydrates, solvates, prodrugs and polymorphs thereof;
wherein
R¹ is selected from the group consisting of $^{18}F$, F and LG;
R² is H or PG;
PG is a protecting group;
LG is a leaving group,
wherein the hydrogen in the formula III are independently selected from $^1H$, $^2H$ and $^3H$.

5. The compound according to item 4, which is

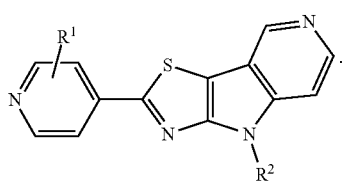

6. The compound according to item 4, which is

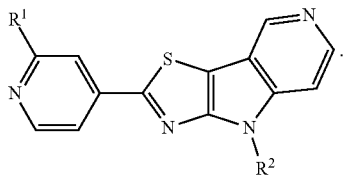

7. The compound according to item 1, 2, 3, 4, 5 or 6 wherein R¹ is $^{18}F$ and R² is H.
8. The compound according to item 1, 2, 3, 4, 5 or 6 wherein R¹ is F and R² is H.
9. The compound according to item 1, 2, 3, 4, 5 or 6 wherein R¹ is LG and R² is H or PG.
10. The compound according to item 1, 2, 3, 4, 5 or 6 wherein R¹ is LG and R² is H.
11. The compound according to item 1, 2, 3, 4, 5 or 6 wherein R¹ is LG and R² is PG.
12. The compound according to item 1, 2, 3, 4, 5, 6, 9, 10 or 11, wherein LG is nitro, halogen or trimethyl ammonium.
13. The compound according to item 12, wherein LG is nitro or trimethyl ammonium.
14. The compound according to item 1, 2, 3, 4, 5, 6, 9, 11, 12 or 13, wherein PG is tert-butyloxycarbonyl (BOC), triphenylmethyl (Trityl) or dimethoxytrityl (DMT).
15. The compound according to item 14, wherein PG is tert-butyloxycarbonyl (BOC).
16. The compound according to item 1, 2, 3, 4, 5 or 6 wherein the compound is detectably labeled.
17. The compound according to item 16, wherein the detectable label is selected from $^2H$, $^3H$ and $^{18}F$.
18. The compound according to item 17, wherein the detectable label is $^{18}F$.
19. A diagnostic composition comprising a compound as defined in any of items 7, 16, 17 or 18 and optionally a pharmaceutically acceptable carrier, diluent, adjuvant or excipient.
20. A compound as defined in item 7 or 18 for use in diagnostics.
21. A compound as defined in item 7 or 18 for use in the imaging of Tau aggregates, particularly for use in positron emission tomography imaging of Tau aggregates.
22. A compound as defined in item 7 or 18 for use in the diagnosis of a disorder associated with Tau aggregates or for use in the diagnosis of a tauopathy, particularly wherein the diagnosis is conducted by positron emission tomography.
23. A compound for use according to item 22, wherein the tauopathy is a 3R tauopathy.
24. A compound for use according to item 22, wherein the tauopathy is a 4R tauopathy.
25. The compound for use according to item 22, wherein the disorder is selected from Alzheimer's disease (AD), familial AD, Creutzfeldt-Jacob disease, dementia pugilistica, Down's Syndrome, Gerstmann-Sträussler-Scheinker disease, inclusion-body myositis, prion protein cerebral amyloid angiopathy, traumatic brain injury (TBI), amyotrophic lateral sclerosis, Parkinsonism-dementia complex of Guam, non-Guamanian motor neuron disease with neurofibrillary tangles, argyrophilic grain disease, corticobasal degeneration (CBD), diffuse neurofibrillary tangles with calcification, frontotemporal dementia with Parkinsonism linked to chromosome 17, Hallervorden-Spatz disease, multiple system atrophy, Niemann-Pick disease type C, pallido-ponto-nigral degeneration, Pick's disease (PiD), progressive subcortical gliosis, progressive supranuclear palsy (PSP), subacute sclerosing panencephalitis, tangle only dementia, postencephalitic Parkinsonism, myotonic dystrophy, Tau panencephalopathy, AD-like with astrocytes, certain prion diseases (GSS with Tau), mutations in LRRK2, chronic traumatic encephalopathy, familial British dementia, familial Danish dementia, frontotemporal lobar degeneration, Guadeloupean Parkinsonism, neurodegeneration with brain iron accumulation, SLC9A6-related mental retardation, white matter tauopathy with globular glial inclusions, traumatic stress syndrome, epilepsy, Lewy body dementia (LBD), hereditary cerebral hemorrhage with amyloidosis (Dutch type), mild cognitive impairment (MCI), multiple sclerosis, Parkinson's disease, atypical parkinsonism, HIV-related dementia, adult onset diabetes, senile cardiac amyloidosis, endocrine tumors, glaucoma, ocular amyloidosis, primary retinal degeneration, macular degeneration (such as age-related macular degeneration (AMD)), optic nerve drusen, optic neuropathy, optic neuritis, and lattice dystrophy; preferably Alzheimer's disease.
26. The compound for use according to item 22, wherein the disorder is selected from Huntington's disease, ischemic stroke and psychosis in AD.
27. The compound for use according to item 22, wherein the disorder is Alzheimer's disease (AD).
28. The compound for use according to any one of items 21 to 27, wherein the Tau aggregates are imaged in the brain or in the eye, preferably wherein the detectable label is $^{18}F$ and the imaging is positron emission tomography.

29. A method of imaging of Tau aggregates, particularly a method of positron emission tomography imaging of Tau aggregates, wherein an effective amount of a compound as defined in item 7 or 18 is administered to a patient.
30. A method of diagnosing a disorder associated with Tau aggregates or a tauopathy, wherein an effective amount of a compound as defined in item 7 or 18 is administered to a patient, particularly wherein the diagnosis is conducted by positron emission tomography.
31. The method according to item 30, wherein the disorder is selected from Alzheimer's disease (AD), familial AD, Creutzfeldt-Jacob disease, dementia pugilistica, Down's Syndrome, Gerstmann-Sträussler-Scheinker disease, inclusion-body myositis, prion protein cerebral amyloid angiopathy, traumatic brain injury, amyotrophic lateral sclerosis, Parkinsonism-dementia complex of Guam, non-Guamanian motor neuron disease with neurofibrillary tangles, argyrophilic grain disease, corticobasal degeneration (CBD), diffuse neurofibrillary tangles with calcification, frontotemporal dementia with Parkinsonism linked to chromosome 17, Hallervorden-Spatz disease, multiple system atrophy, Niemann-Pick disease type C, pallido-ponto-nigral degeneration, Pick's disease (PiD), progressive subcortical gliosis, progressive supranuclear palsy (PSP), subacute sclerosing panencephalitis, tangle only dementia, postencephalitic Parkinsonism, myotonic dystrophy, Tau panencephalopathy, AD-like with astrocytes, certain prion diseases (GSS with Tau), mutations in LRRK2, chronic traumatic encephalopathy, familial British dementia, familial Danish dementia, frontotemporal lobar degeneration, Guadeloupean Parkinsonism, neurodegeneration with brain iron accumulation, SLC9A6-related mental retardation, white matter tauopathy with globular glial inclusions, traumatic stress syndrome, epilepsy, Lewy body dementia (LBD), hereditary cerebral hemorrhage with amyloidosis (Dutch type), mild cognitive impairment (MCI), multiple sclerosis, Parkinson's disease, atypical parkinsonism, HIV-related dementia, adult onset diabetes, senile cardiac amyloidosis, endocrine tumors, glaucoma, ocular amyloidosis, primary retinal degeneration, macular degeneration (such as age-related macular degeneration (AMD)), optic nerve drusen, optic neuropathy, optic neuritis, and lattice dystrophy; preferably Alzheimer's disease.
32. The method according to item 30, wherein the disorder is selected from Huntington's disease, ischemic stroke and psychosis in AD.
33. The method according to item 30, wherein the disorder is Alzheimer's disease (AD).
34. The method according to any one of items 29 to 33, wherein the Tau aggregates are imaged in the brain or in the eye, preferably wherein the detectable label is $^{18}F$ and the imaging is positron emission tomography.
35. Use of the compound according to item 8 as an analytical reference.
36. Use of the compound according to item 8 as an in vitro screening tool.
37. A method of preparing a compound as defined in item 7 comprising reacting a compound as defined in item 9 with a [$^{18}F$]fluorinating agent, wherein the method further comprises cleaving of the protecting group PG, if present.
38. The method according to item 37, wherein the [$^{18}F$] fluorinating agent is selected from $K^{18}F$, $H^{18}F$, $Cs^{18}F$, $Na^{18}F$ and a tetra($C_{1-6}$ alkyl) ammonium salt of $^{18}F$.
39. A kit for preparing a radiopharmaceutical preparation, said kit comprising a sealed vial containing a predetermined quantity of a compound as defined in item 9.
40. The kit according to item 39, which further comprises at least one component selected from a reaction solvent, a solid-phase extraction cartridge, a reagent for cleaving the protecting group, a solvent for purification, a solvent for formulation and a pharmaceutically acceptable carrier, diluent, adjuvant or excipient for formulation.
41. A method of collecting data for the diagnosis of a disorder associated with tau aggregates in a sample or a patient comprising:
    (a) bringing a sample or a specific body part or body area suspected to contain a tau aggregate into contact with a compound as defined in items 16 to 18;
    (b) allowing the compound to bind to the tau aggregate;
    (c) detecting the compound bound to the tau aggregate; and
    (d) optionally correlating the presence or absence of compound binding with the tau aggregate with the presence or absence of tau aggregate in the sample or specific body part or body area.
42. A method of collecting data for determining a predisposition to a disorder associated with tau aggregates in a patient comprising detecting the specific binding of a compound as defined in items 16 to 18 to a tau aggregate in a sample or in situ which comprises the steps of:
    (a) bringing the sample or a specific body part or body area suspected to contain the tau aggregate into contact with the compound as defined in items 13 to 15, which compound specifically binds to the tau aggregate;
    (b) allowing the compound to bind to the tau aggregate to form a compound/tau aggregate complex;
    (c) detecting the formation of the compound/tau aggregate complex;
    (d) optionally correlating the presence or absence of the compound/tau aggregate complex with the presence or absence of tau aggregate in the sample or specific body part or body area; and
    (e) optionally comparing the amount of the compound/tau aggregate to a normal control value.
43. A method of collecting data for predicting responsiveness of a patient suffering from a disorder associated with tau aggregates and being treated with a medicament comprising:
    (a) bringing a sample or a specific body part or body area suspected to contain an tau aggregate into contact with a compound as defined in items 16 to 18, which compound specifically binds to the tau aggregate;
    (b) allowing the compound to bind to the tau aggregate to form a compound/tau aggregate complex;
    (c) detecting the formation of the compound/tau aggregate complex;
    (d) optionally correlating the presence or absence of the compound/tau aggregate complex with the presence or absence of tau aggregate in the sample or specific body part or body area; and
    (e) optionally comparing the amount of the compound/tau aggregate to a normal control value.

It is understood that the present invention covers compounds of the formula (II) and formula (III) in which one or more of the respective atoms is replaced by a different isotope. For instance, the compounds of the formula (II) and formula (III) include compounds in which one or more of the hydrogen atoms is replaced by tritium and/or one or more of the hydrogen atoms is replaced by deuterium.

The present inventors have surprisingly found that the compounds of the formula (II) and formula (III) in which $R^1$ is $^{18}F$ or F and $R^2$ is H (compounds F-2 and $^{18}F$-2, F-3 and <sup>18</sup>F-3, respectively) have significantly improved properties compared to the prior art compound <sup>18</sup>F-1.

F-2

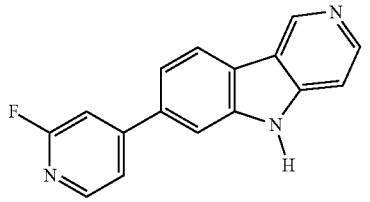

<sup>18</sup>F-2

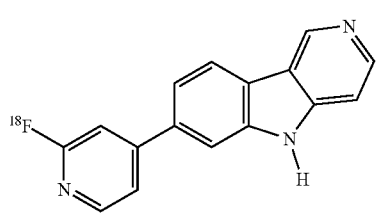

F-3

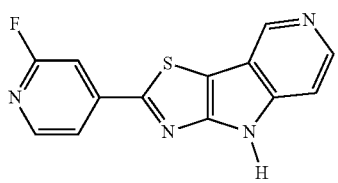

<sup>18</sup>F-3

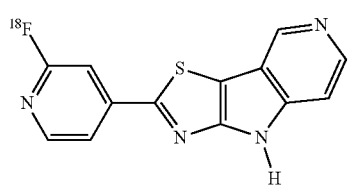

DETAILED DESCRIPTION

The present invention relates to detectably labeled compounds of the formula (II) and formula (III)

(II)

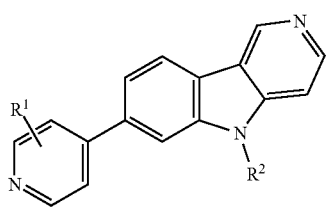

(III)

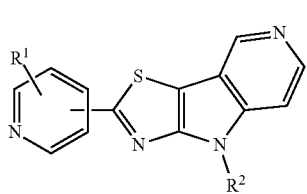

Preferred compounds of the present invention are and

A further preferred compound is

.

More preferred compounds are

Further more preferred compounds are

.

Even more preferred compounds of the present invention are and

-continued

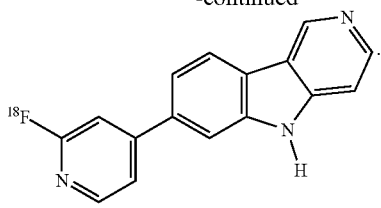

Other even more preferred compounds of the present invention are

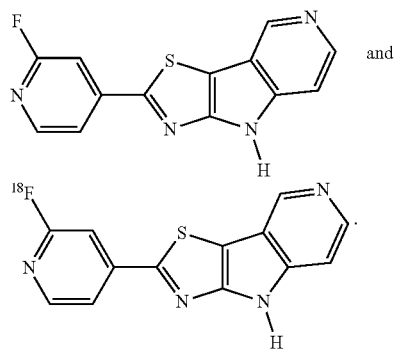

and

An even more preferred compound of the present invention is

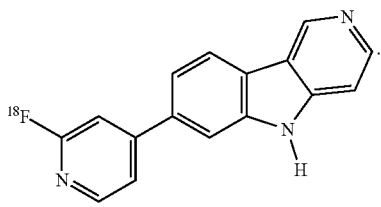 [SMILES: [18F]c1cc(-c2ccc3c(c2)[nH]c2ccncc23)ccn1]

Another even more preferred compound of the present invention is

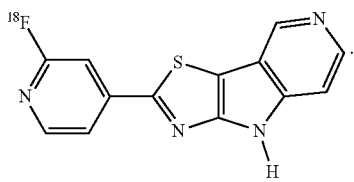 [SMILES: [18F]c1cc(-c2nc3[nH]c4ccncc4c3s2)ccn1]

Detectably labeled compounds of the present invention can be employed in the selective detection of disorders and abnormalities associated with Tau aggregates such as Alzheimer's disease and other tauopathies, for example, by using Positron Emission Tomography (PET) imaging. The present invention also refers to intermediates which can be used in the production of such imaging compounds. The present compounds have a high affinity for Tau and since they have a low affinity for amyloid-beta, MAO A and MAO B they can be used as highly selective molecular probes for binding pathological Tau and thus avoid detection of other pathologies and misdiagnosis.

The detectably labeled compounds of the present invention (in particular $^{18}$F-2) also lead to a low signal in healthy brain, so that they can reduce background signal interference and thus provide a low detection limit.

Due to their good brain uptake, fast washout from healthy brain and low long-term retention in healthy brain the detectably labeled compounds of the present invention (in particular $^{18}$F-2 and $^{18}$F-3) provide a good signal-to-noise ratio.

Furthermore, labeling with e.g. $^{18}$F, is possible in high yields.

Definitions

The term "alkyl" refers to a saturated straight or branched carbon chain, which, unless specified otherwise, contain from 1 to 6 carbon atoms.

"Hal" or "halogen" represents F, Cl, Br and I. Preferably, "halogen" is, independently in each occurrence, selected from F, Cl and Br, more preferably, from F and Cl, even more preferably F.

The terms "protecting group" (PG) and "amine protecting group" as employed herein is any protecting group which is suitable for protecting an amine group during an envisaged chemical reaction. Examples of suitable protecting groups are well-known to a person skilled in the art. Suitable protecting groups are discussed, e.g., in the textbook Greene and Wuts, Protecting groups in Organic Synthesis, third edition, page 494-653, which is included herein by reference. Protecting groups can be chosen from carbamates, amides, imides, N-alkyl amines, N-aryl amines, imines, enamines, boranes, N-P protecting groups, N-sulfenyl, N-sulfonyl and N-silyl. Specific preferred examples of protecting groups (PG) are carbobenzyloxy (Cbz), p-methoxybenzyl carbonyl (Moz or MeOZ), tert-butyloxycarbonyl (BOC), 9-fluorenylmethyloxycarbonyl (FMOC), benzyl (Bn), p-methoxybenzyl (PMB), 3,4-dimethoxybenzyl (DMPM), p-methoxyphenyl (PMP), triphenylmethyl (Trityl), methoxyphenyl diphenylmethyl (MMT), or dimethoxytrityl (DMT). More preferred examples of the protecting group PG include tert-butyloxycarbonyl (BOC), dimethoxytrityl (DMT) and triphenylmethyl (Trityl). One more preferred example of the protecting group PG is tert-butyloxycarbonyl (BOC).

The term "leaving group" (LG) as employed herein is any leaving group and means an atom or group of atoms can be replaced by another atom or group of atoms. Examples are given e.g. in Synthesis (1982), p. 85-125, table 2, Carey and Sundberg, Organische Synthese, (1995), page 279-281, table 5.8; or Netscher, Recent Res. Dev. Org. Chem., 2003, 7, 71-83, scheme 1, 2, 10 and 15 and others). (Coenen, Fluorine-18 Labeling Methods: Features and Possibilities of Basic Reactions, (2006), in: Schubiger P. A., Friebe M., Lehmann L., (eds), PET-Chemistry—The Driving Force in Molecular Imaging. Springer, Berlin Heidelberg, pp. 15-50, explicitly: scheme 4 pp. 25, scheme 5 pp 28, table 4 pp 30, FIG. 7 pp 33). Preferably, the "leaving group" (LG) is nitro, halogen or trimethyl ammonium. More preferably, "leaving group" (LG) is nitro or trimethyl ammonium. In one preferred embodiment, "leaving group" (LG) is nitro. In another preferred embodiment, "leaving group" (LG) is trimethyl ammonium.

The term "crown ether" as employed herein means chemical compounds that consist of a ring containing several ether groups. More specifically, the term "crown ether" refers to preferably monocyclic organic groups which may be substituted and contain from 8 to 16 carbon atoms and from 4 to 8 heteroatoms selected from N, O and S in the ring. Each of the one or more optional substituents may be independently selected from any organic group containing from 1 to 15 carbon atoms and optionally 1 to 6 heteroatoms selected from N, O and S. Preferred examples of the "crown ether" are optionally substituted monocyclic rings containing 10 to 14 carbon atoms and 5 to 7 heteroatoms selected from N, O and S in the ring. Examples of the "crown ether" are optionally substituted monocyclic rings containing 12 carbon atoms and 6 heteroatoms selected from N and O in the ring. Specific examples include 18-crown-6, dibenzo-18-crown-6, and diaza-18-crown-6.

The term "cryptand" as employed herein relates to a class of polycyclic compounds related to the crown ethers, having three chains attached at two nitrogen atoms. A well-known "cryptand" is 4,7,13,16,21,24-hexaoxa-1,10-diazabicyclo[8.8.8]hexacosane (Kryptofie).

Tau as used herein refers to a highly soluble microtubule binding protein mostly found in neurons and includes the major 6 isoforms, cleaved or truncated forms, and other modified forms such as arising from phosphorylation, glycosylation, glycation, prolyl isomerization, nitration, acetylation, polyamination, ubiquitination, sumoylation and oxidation. Pathologic Tau or Tau aggregates (Neurofibrillary Tangles, NFTs) as used herein refer to insoluble aggregates of the hyperphosphorylated Tau protein containing paired helical filaments and straight filaments. Their presence is a hallmark of AD and other diseases known as tauopathies.

The tau gene contains 16 exons with the major tau protein isoforms being encoded by 11 of them The alternative splicing of exon 10 generates tau isoforms with either three (exon 10 missing) or four (exon 10 present) repeat domains, known as 3R and 4R tau, respectively (A. Andreadis et al., Biochemistry 31, (1992) 10626-10633; M. Tolnay et al., IUBMB Life, 55(6): 299-305, 2003). In Alzheimer's disease, the ratio of 3R and 4R isoforms is similar. In contrast thereto, in some tauopathies one of the two isoforms is predominantly present. Herein, the term "3R tauopathy" refers to tauopathies (such as Pick's disease (PiD)) in which the 3R isoform is predominantly present. Herein, the term "4R tauopathy" refers to tauopathies (such as progressive supranuclear palsy (PSP) and corticobasal degeneration (CBD)) in which the 4R isoform is predominantly present.

The term "polymorphs" refers to the various crystalline structures of the compounds of the present invention. This may include, but is not limited to, crystal morphologies (and amorphous materials) and all crystal lattice forms. Salts of the present invention can be crystalline and may exist as more than one polymorph.

Solvates, hydrates as well as anhydrous forms of the present compounds are also encompassed by the invention. The solvent included in the solvates is not particularly limited and can be any pharmaceutically acceptable solvent. Examples include water and $C_{1-4}$ alcohols (such as methanol or ethanol).

As used hereinafter in the description of the invention and in the claims, the term "prodrug" means any covalently bonded compound which releases the active parent pharmaceutical due to in vivo biotransformation. The reference by Goodman and Gilman (The Pharmacological Basis of Therapeutics, 8 ed, McGraw-Hill, Int. Ed. 1992, "Biotransformation of Drugs", p 13-15) describing prodrugs generally is hereby incorporated herein by reference.

As used hereinafter in the description of the invention and in the claims, the term "pharmaceutically acceptable salt" relates to non-toxic derivatives of the disclosed compounds wherein the parent compound is modified by making salts of inorganic and organic acids thereof. Inorganic acids include, but are not limited to, acids such as hydrochloric, nitric or sulfuric acid. Organic acids include, but are not limited to, carboxylic and sulfonic acids such as aliphatic, cycloaliphatic, aromatic, araliphatic and heterocyclic acids. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two. Lists of suitable salts can be found in Remington's Pharmaceutical Sciences, 18th ed., Mack Publishing Company, Easton, Pa., 1990, p. 1445, the disclosure of which is hereby incorporated by reference.

"Pharmaceutically acceptable" is defined as those compounds, materials, compositions, and/or dosage forms which are, within the scope of sound medical judgment, suitable for use in contact with the tissues of human beings and animals without excessive toxicity, irritation, allergic response, or other problem or complication commensurate with a reasonable benefit/risk ratio.

The patients or subjects in the present invention are typically animals, particularly mammals, more particularly humans.

The preferred definitions given in the "Definition"-section apply to all of the embodiments described herein unless stated otherwise.

Diagnostic Procedures

The detectably labeled compounds of the present invention (in particular $^{18}$F-2 and $^{18}$F-3) are particularly suitable for imaging of Tau protein aggregates. With respect to Tau protein, the detectably labeled compounds of the present invention (in particular $^{18}$F-2 and $^{18}$F-3) are able to bind to various types of Tau aggregates such as pathologically aggregated Tau, hyperphosphorylated Tau, neurofibrillary tangles, paired helical filaments, straight filaments, neurotoxic soluble oligomers, polymers and fibrils.

Due to the above binding characteristics, the detectably labeled compounds of the present invention (in particular $^{18}$F-2 and $^{18}$F-3) are suitable for use in the diagnosis of disorders associated with Tau aggregates. The detectably labeled compounds of the present invention (in particular $^{18}$F-2 and $^{18}$F-3) are particularly suitable for positron emission tomography (PET) imaging of Tau deposits. Typically $^{18}$F labeled compounds of the formula (II) and formula (III) are employed as detectably labeled compounds if the compounds are to be administered to a patient.

In the imaging of Tau aggregates a detectably labeled compound of the formula (II) (preferably $^{18}$F-2) and formula (III) (preferably $^{18}$F-3) is administered and the signal stemming from the compound that is specifically bound to the Tau aggregates is detected. The specific binding is a result of the high binding affinity of the compounds of the formula (II) and formula (III) to the Tau aggregates.

If no signal stemming from the detectable label is detected then the instant method can be used to exclude a tauopathy, which indicates that a neurological disorder other than a tauopathy is present.

In the methods of diagnosing a disorder associated with Tau protein aggregates such as Alzheimer's disease, or a predisposition therefor in a subject, the method comprising:
a) administering to the mammal a diagnostically effective amount of a detectably labeled compound of the present invention (in particular $^{18}$F-2 and $^{18}$F-3);
b) allowing the detectably labeled compound of the present invention (in particular $^{18}$F-2 and $^{18}$F-3) to distribute into the tissue of interest (such as brain tissue, the eye or body fluids such as cerebrospinal fluid (CSF)); and c) imaging the tissue of interest, wherein an increase in binding of the detectably labeled compound of the present invention (in particular $^{18}$F-2 and $^{18}$F-3) to the tissue of interest compared to a normal control level of binding indicates that the subject is suffering from or is at risk of developing a disorder associated with Tau protein aggregates.

The detectably labeled compounds of the present invention (in particular $^{18}$F-2 and $^{18}$F-3) can be used for imaging of Tau protein aggregates in any sample or a specific body part or body area of a patient which suspected to contain a Tau protein aggregate. The detectably labeled compounds of the present invention (in particular $^{18}$F-2 and $^{18}$F-3) are able to pass the blood-brain barrier and to pass into the eye. Consequently, they are particularly suitable for imaging of Tau protein aggregates in the brain, in the eye (ophthalmic and/or retinal imaging) as well as in body fluids such as cerebrospinal fluid (CSF).

In diagnostic applications, the detectably labeled compounds of the present invention (in particular $^{18}$F-2 and $^{18}$F-3) are preferably administered in a diagnostic composition.

Diagnosis of a Tau disorder or of a predisposition to a Tau-associated disorder in a patient may be achieved by detecting the specific binding of a detectably labeled compound of the present invention (in particular $^{18}$F-2 and $^{18}$F-3) to the Tau protein aggregates in a sample or in situ, which includes:

(a) bringing the sample or a specific body part or body area suspected to contain the Tau protein aggregate into contact with a detectably labeled compound of the present invention (in particular $^{18}$F-2 and $^{18}$F-3) which binds the Tau protein aggregate;

(b) allowing the detectably labeled compound of the present invention (in particular $^{18}$F-2 and $^{18}$F-3) to bind to the Tau protein aggregate to form a compound/Tau protein aggregate complex (hereinafter "compound/Tau protein aggregate complex" will be abbreviated as "compound/protein aggregate complex");

(c) detecting the formation of the compound/protein complex, (d) optionally correlating the presence or absence of the compound/protein complex with the presence or absence of Tau protein aggregates in the sample or specific body part or area; and (e) optionally comparing the amount of the compound/protein to a normal control value, wherein an increase in the amount of the compound/protein compared to a normal control value may indicate that the patient is suffering from or is at risk of developing a Tau-associated disorder.

After the sample or a specific body part or body area has been brought into contact with the detectably labeled compound of the present invention (in particular $^{18}$F-2 and $^{18}$F-3), the compound is allowed to bind to the Tau protein aggregate. The amount of time required for binding will depend on the type of test (e.g., in vitro or in vivo) and can be determined by a person skilled in the field by routine experiments.

The compound which has bound to the Tau protein aggregate can be subsequently detected by any appropriate method. A preferred method is positron emission tomography (PET).

The presence or absence of the compound/protein is then optionally correlated with the presence or absence of Tau protein aggregates in the sample or specific body part or area. Finally, the amount of the compound/protein can be compared to a normal control value which has been determined in a sample or a specific body part or body area of a healthy subject, wherein an increase in the amount of the compound/protein compared to a normal control value may indicate that the patient is suffering from or is at risk of developing a Tau-associated disorder.

Predicting responsiveness of a patient suffering from a disorder associated with Tau protein aggregates and being treated with a medicament can be achieved by (a) bringing a sample or a specific body part or body area suspected to contain a Tau protein aggregate into contact with a detectably labeled compound of the present invention (in particular $^{18}$F-2 and $^{18}$F-3);

(b) allowing the detectably labeled compound of the present invention (in particular $^{18}$F-2 and $^{18}$F-3) to bind to the Tau protein aggregate to form a compound/protein aggregate complex;

(c) detecting the formation of the compound/protein aggregate complex;

(d) optionally correlating the presence or absence of the compound/protein aggregate complex with the presence or absence of Tau protein aggregate in the sample or specific body part or body area; and (e) optionally comparing the amount of the compound/protein aggregate to a normal control value.

How steps (a) to (e) can be conducted has already been explained above.

In the method for predicting responsiveness the amount of the compound/protein complex can be optionally compared at various points of time during the treatment, for instance, before and after onset of the treatment or at various points of time after the onset of the treatment. A change, especially a decrease, in the amount of the compound/protein complex may indicate that the patient has a high potential of being responsive to the respective treatment.

A compound according to the present invention can also be incorporated into a test kit for detecting a Tau protein aggregate. The test kit typically comprises a container holding one or more compounds according to the present invention and instructions for using the compound for the purpose of binding to a Tau protein aggregate to form a compound/protein complex and detecting the formation of the compound/protein complex such that presence or absence of the compound/protein complex correlates with the presence or absence of the Tau protein aggregates.

The term "test kit" refers in general to any diagnostic kit known in the art. More specifically, the latter term refers to a diagnostic kit as described in Zrein et al., Clin. Diagn. Lab. Immunol., 1998, 5, 45-49.

Diagnostic Compositions

A "diagnostic composition" is defined in the present invention as a composition comprising a detectably labeled compound of the present invention (preferably $^{18}$F labeled; in particular $^{18}$F-2 and $^{18}$F-3). For in vivo applications the diagnostic composition should be in a form suitable for administration to mammals such as humans. Preferably a diagnostic composition further comprises a physiologically acceptable carrier, diluent, adjuvant or excipient. Administration to a patient is preferably carried out by injection of the composition as an aqueous solution. Such a composition may optionally contain further ingredients such as solvents, buffers; pharmaceutically acceptable solubilizers; and pharmaceutically acceptable stabilizers or antioxidants.

Pharmaceutically acceptable excipients are well known in the pharmaceutical art, and are described, for example, in Remington's Pharmaceutical Sciences, 15$^{th}$ Ed., Mack Publishing Co., New Jersey (1975). The pharmaceutical excipient can be selected with regard to the intended route of administration and standard pharmaceutical practice. The excipient must be acceptable in the sense of being not deleterious to the recipient thereof.

If the detectably labeled compounds of the present invention (preferably $^{18}$F labeled, in particular $^{18}$F-2 and $^{18}$F-3) are administered parenterally, then examples of such administration include one or more of: intravenously, intraarterially, intraperitoneally, intrathecally, intraventricularly, intraurethrally, intrasternally, intracranially, intramuscularly or subcutaneously administering the compounds; and/or by using infusion techniques. For parenteral administration, the compounds are best used in the form of a sterile aqueous solution which may contain other excipients. The aqueous solutions should be suitably buffered (preferably to a pH of from 3 to 9), if necessary. The preparation of suitable parenteral formulations under sterile conditions is readily accomplished by standard pharmaceutical techniques well known to those skilled in the art.

The dose of the detectably labeled compounds of the present invention (preferably $^{18}$F labeled, in particular $^{18}$F-2 and $^{18}$F-3) will vary depending on the exact compound to be administered, the weight of the patient, size and type of the sample, and other variables as would be apparent to a physician skilled in the art. Generally, the dose could preferably lie in the range 0.001 µg/kg to 10 µg/kg, preferably 0.01 µg/kg to 1.0 µg/kg. The radioactive dose can be, e.g., 100 to 600 MBq, more preferably 150 to 450 MBq.

The diagnostic compositions of the invention can be produced in a manner known per se to the skilled person as described, for example, in Remington's Pharmaceutical Sciences, 15$^{th}$ Ed., Mack Publishing Co., New Jersey (1975).

For instance, the compounds of the present invention can be employed in a liposomal composition as described in WO 2016/057812A1 which comprises a compound of formula (II) and formula (III) as a ligand for use in the selective detection of disorders and abnormalities associated with Tau aggregates by nonradioactive magnetic resonance imaging (MRI).

General Synthesis of $^{18}$F-Labeled Compounds of the Present Invention

Compounds having the formula (II) and formula (III) which are labeled by $^{18}$F can be prepared by reacting a compound of formula (II) and formula (III), in which R$^1$ is LG and R$^2$ is H or PG, with an $^{18}$F-fluorinating agent, so that the leaving group LG is replaced by $^{18}$F. The preparation includes the cleavage of the protecting group PG, if present.

Any suitable $^{18}$F-fluorinating agent can be employed. Typical examples include H$^{18}$F, alkali or alkaline earth $^{18}$F-fluorides (e.g., K$^{18}$F, Rb$^{18}$F, Cs$^{18}$F, and Na$^{18}$F). Optionally, the $^{18}$F-fluorination agent can be used in combination with a chelating agent such as a cryptand (e.g.: 4,7,13,16,21,24-hexaoxa-1,10-diazabicyclo[8.8.8]-hexacosane—Kryptofix®) or a crown ether (e.g.: 18-crown-6). Alternatively, the $^{18}$F-fluorinating agent can be a tetraalkyl ammonium salt of $^{18}$F or a tetraalkyl phosphonium salt of $^{18}$F; e.g., tetra(C$_{1-6}$ alkyl)ammonium salt of $^{18}$F or a tetra(C$_{1-6}$ alkyl)phosphonium salt of $^{18}$F. Examples thereof include tetrabutyl ammonium [$^{18}$F]fluoride and tetrabutyl phosphonium [$^{18}$F]fluoride. Preferably, the $^{18}$F-fluorination agent is K$^{18}$F, H$^{18}$F, Cs$^{18}$F, Na$^{18}$F or tetrabutyl ammonium [$^{18}$F]fluoride.

The reagents, solvents and conditions which can be used for the $^{18}$F-fluorination are well-known to a person skilled in the field (L. Cai, S. Lu, V. Pike, Eur. J. Org. Chem 2008, 2853-2873; J. Fluorine Chem., 27 (1985):177-191; Coenen, Fluorine-18 Labeling Methods: Features and Possibilities of Basic Reactions, (2006), in: Schubiger P. A., Friebe M., Lehmann L., (eds), PET-Chemistry—The Driving Force in Molecular Imaging. Springer, Berlin Heidelberg, pp. 15-50). Preferably, the solvents used in the $^{18}$F-fluorination are DMF, DMSO, acetonitrile, DMA, or mixtures thereof, preferably the solvent is acetonitrile or DMSO.

If desired, the compound having the formula (II) and formula (III) can have R$^1$ is LG and R$^2$ is PG, wherein the protecting group PG protects the amine during the $^{18}$F-fluorination reaction. This amine protecting group can be subsequently removed. Methods for removing the amine protecting group are known in the art and include, but are not limited to, acidic cleavage.

If desired, the compound of formula (II) and formula (III) can be isolated and/or purified further before use. Corresponding procedures are well-known in the art.

The precursor compounds having the formula (II) and formula (III) in which R$^1$ is LG and R$^2$ is H or PG can be provided in a kit which is suitable for producing the compounds of the formula (II) and formula (III) by reaction with a $^{18}$F-fluorinating agent. In one embodiment the kit comprises a sealed vial containing a predetermined quantity of the precursor compound of the present invention. For instance, the kit can contain 1.5 to 75 µmol, preferably 7.5 to 50 µmol, more preferably 10 to 30 µmol of a precursor compound (II) or precursor compound (III) of the present invention. Optionally, the kit can contain further components, such as a reaction solvent, a solid-phase extraction cartridge, a reagent to obtain the $^{18}$F-fluorinating agent, a reagent for cleaving the protecting group, a solvent for purification, a solvent for formulation and a pharmaceutically acceptable carrier, diluent, adjuvant or excipient for formulation.

The compounds of the present invention in which R$^1$ is F and R$^2$ is H can be used as an analytical reference or an in vitro screening tool.

The compounds of the present invention in which R$^1$ is F and R$^2$ is H can be used as an analytical reference for the quality control and release of a compound of the present invention in which R$^1$ is $^{18}$F and R$^2$ is H.

The compounds of the present invention in which R$^1$ is F and R$^2$ is H can be used as an in vitro screening tool for characterization of tissue with Tau pathology and for testing of compounds targeting Tau pathology on such tissue.

The present invention illustrated by the following examples which should not be construed as limiting.

EXAMPLES

All reagents and solvents were obtained from commercial sources and used without further purification. Proton ($^1$H) spectra were recorded on a Bruker DRX-400 MHz NMR spectrometer or on a Bruker AV-400 MHz NMR spectrometer in deuterated solvents. Mass spectra (MS) were recorded on an Advion CMS mass spectrometer. Chromatography was performed using silica gel (Fluke: Silica gel 60, 0.063-0.2 mm) and suitable solvents as indicated in the specific examples. Flash purification was conducted with a Biotage Isolera One flash purification system using HP-Sil (Biotage) or puriFlash-columns (Interchim) and the solvent gradient indicated in the specific examples. Thin layer chromatography (TLC) was carried out on silica gel plates with UV detection.

Although some of the present examples do not indicate that the respective compounds were detectably labeled, it is understood that corresponding detectably labeled compounds can be easily prepared, e.g., by using detectably labeled starting materials, such as starting materials containing ³H atoms.

Abbreviations

| | |
|---|---|
| AD | Alzheimer's disease |
| Boc, BOC | tert-butyloxycarbonyl |
| CBD | corticobasal degeneration |
| d.c. | corrected for decay |
| d | doublet |
| dd | doublet of doublet |
| DMF | N,N-dimethyl formamide |
| DMSO | dimethylsulfoxide |
| EI | electron ionisation |
| ELSD | evaporative light scattering detector |
| ESI | electrospray ionisation |
| FTD | Frontotemporal dementia |
| HPLC | high performance liquid chromatography |
| HC | Healthy control |
| GBq | Gigabequerel |
| $K_{222}$ | 4, 7, 13, 16, 21, 24-hexaoxa-1,10-diazabicyclo[8.8.8]-hexacosane (Kryptofix 222) |
| MBq | Megabequerel |
| MS | mass spectrometry |
| MeCN | acetonitrile |
| m | multiplet |
| mc | centered multiplet |
| n.c.a. | non-carrier-added |
| n.d.c. | not decay corrected |
| NMR | nuclear magnetic resonance spectroscopy : chemical shifts (δ) are given in ppm. |
| PET | Positron-Emission-Tomography |
| PiD | Pick's disease |
| PSP | progressive supranuclear palsy |
| q | quadruplet (quartet) |
| RT | room temperature |
| s | singulet |
| t | triplet |
| Tau | Tau protein, Tau deposits, Tau aggregates |
| TBI | Traumatic brain injury |
| TLC | thin layer chromatography |

Preparative Example A

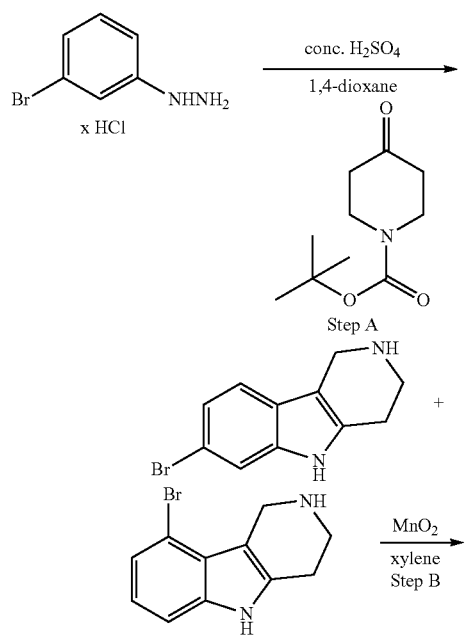

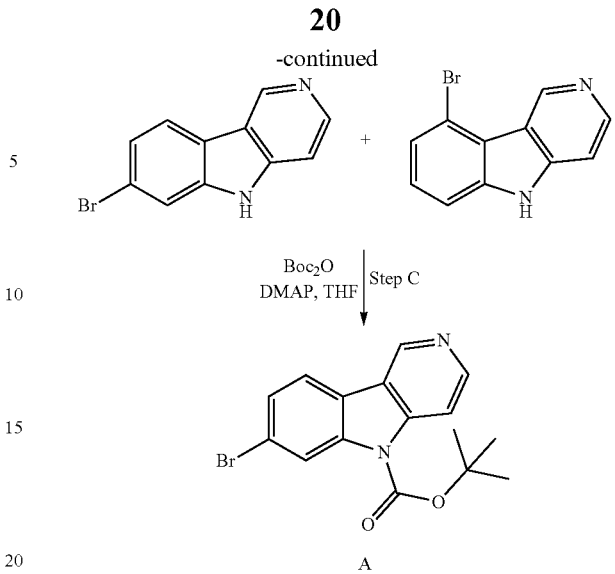

Step A

Commercially available 3-bromophenylhydrazine hydrochloride (1.4 g, 6.26 mmol) and tert-butyl 4-oxopiperidine-1-carboxylate (1.25 g, 6.26 mmol) were dissolved in 1,4-dioxane (40 mL) and the reaction mixture cooled at 0° C. Then concentrated sulfuric acid (4 mL) was added dropwise, the mixture was stirred at room temperature for 10 minutes and then refluxed overnight. The mixture was cooled to room temperature and the 1,4-dioxane was removed under reduced pressure. The residue was cooled to 0° C. and a 6 M aqueous sodium hydroxide solution was added dropwise until pH-13 was reached. The aqueous layer was extracted with dichloromethane (3×50 mL), the organics were combined, dried over $Na_2SO_4$, filtered and concentrated under reduced pressure. The residue was purified on HP-Sil SNAP cartridges using a Biotage Isolera One purification system by employing a dichloromethane/methanol gradient (100/0-→80/20) to obtain a mixture of regioisomers (1.1 g, 70%).

MS (ESI): m/z=251.23/253.25 [M+H]⁺

Step B

To a solution of the mixture of regioisomers from Step A above (1.1 g, 4.4 mmol) in xylene (20 mL) was added manganese(IV)-oxide (3.80 g, 40 mmol). The mixture was stirred at 110° C. (internal temperature) overnight. The solid material ($MnO_2$) was filtered off through a paper filter, and the solvents were removed under reduced pressure. The residue was purified on HP-Sil cartridges, by employing a dichloromethane/methanol gradient (100/0-→90/10) to obtain a mixture of regioisomers (0.47 g, 43%)

MS (ESI): m/z=247.19/249.18 [M+H]⁺

Step C

The mixture of regioisomers from Step B above (0.47 g, 1.89 mmol) was dissolved in tetrahydrofurane (10 mL) and di-tert-butyldicarbonat (0.265 g, 2.43 mmol) was added followed by 4-(dimethylamino)-pyridine (0.019 g, 0.16 mmol). The reaction mixture was stirred at room temperature overnight, and the solvent removed under reduced pressure. The residue was purified on HP-Sil SNAP cartridges using a Biotage Isolera One purification system employing an ethyl acetate/n-heptane gradient (0/100-→50/50) to afford the more polar title compound (0.238 g, 36%).

¹H-NMR (400 MHz, $CDCl_3$) δ=9.18 (s, 1H), 8.63 (d, 1H), 8.49 (d, 1H), 8.07 (d, 1H), 7.83 (d, 1H), 7.49 (dd, 1H), 1.79 (s, 9H)

MS (ESI): m/z=347.11/349.11 [M+H]⁺

Example 1

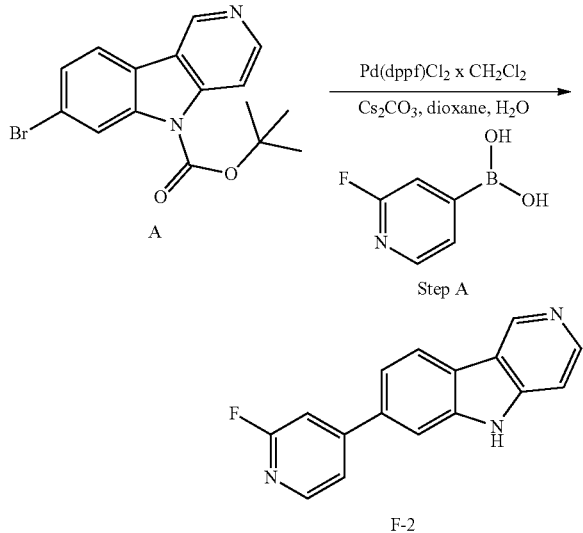

Step A

Step A

To a mixture of degassed 1,4-dioxane (3.1 mL) and water (0.72 mL) in a microwave vial was added [1,1'-bis(diphenylphosphino)ferrocene]dichloropalladium(II) complex with dichloromethane (0.006 g, 0.0072 mmol), followed by the title compound from Preparative Example A (0.05 g, 0.144 mmol), (2-fluoropyridin-4-yl)boronic acid (0.025 g, 0.176 mmol) and cesium carbonate (0.096 g, 0.29 mmol). The reaction mixture was then heated at ~115° C. in a sand-bath for 6 hours. The reaction mixture was diluted with ethyl acetate (60 mL) and water (20 mL), the organic phase was separated, dried over Na₂SO₄, filtered and the solvents were evaporated in vacuo. The dark residue was purified by chromatography on silica (12 g, puriFlash, Interchim) using a Biotage Isolera system employing a dichloromethane/methanol gradient (100/0-→95/5-→90/10-→80/20) to afford the title compound F-2 as beige solid (0.0099 g, 26%).

¹H-NMR (400 MHz, DMSO-d₆) δ=11.92 (br-s, 1H), 9.42 (s, 1H), 8.47 (d, 1H), 8.39 (d, 1H), 8.34 (d, 1H), 8.01 (s, 1H), 7.82 (d, 1H), 7.77 (d, 1H), 7.64 (s, 1H), 7.52 (d, 1H)

MS (ESI): m/z=263.71 [M+H]⁺

Example 2

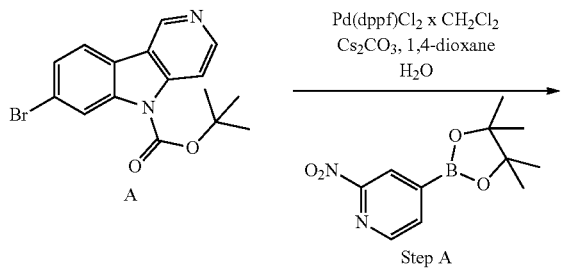

Step A

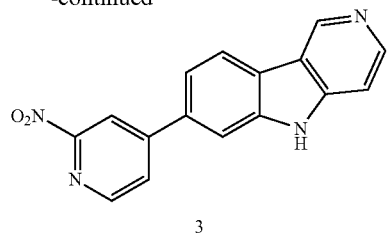

3

Step A

To a mixture of degassed 1,4-dioxane (4.6 mL) and water (1.1 mL) in a microwave vial was added [1,1'-bis(diphenylphosphino)ferrocene]dichloropalladium(II) complex with dichloromethane (0.009 g, 0.0108 mmol), followed by the title compound from Preparative Example A (0.075 g, 0.216 mmol), 2-nitro-4-(4,4,5,5-tetramethyl-1,3,2-dioxaborolan-2-yl)pyridine (0.066 g, 0.264 mmol) and cesium carbonate (0.144 g, 0.435 mmol). The reaction mixture was then heated at ~120° C. in a sand-bath for 6 hours. The reaction mixture was diluted with ethyl acetate (60 mL) and water (20 mL), the organic phase was separated, dried over Na₂SO₄, filtered and the solvents were evaporated in vacuo. The dark residue was purified by chromatography on silica (12 g pufiFlash-column, Interchim) using a Biotage Isolera system employing a dichloromethane/methanol gradient (100/0-→95/5-→90/10-→80/20) to afford the title compound 3 as yellow solid (0.022 g, 35%).

¹H-NMR (400 MHz, DMSO-d₆) δ=11.94 (br-s, 1H), 9.44 (s, 1H), 8.76 (d, 1H); 8.67 (d, 1H), 8.48 (d, 1H), 8.44 (d, 1H), 8.35 (dd, 1H); 8.12 (d, 1H), 7.86 (dd, 1H), 7.54 (dd, 1H)

MS (ESI): m/z=291.69 [M+H]⁺.

Example 3

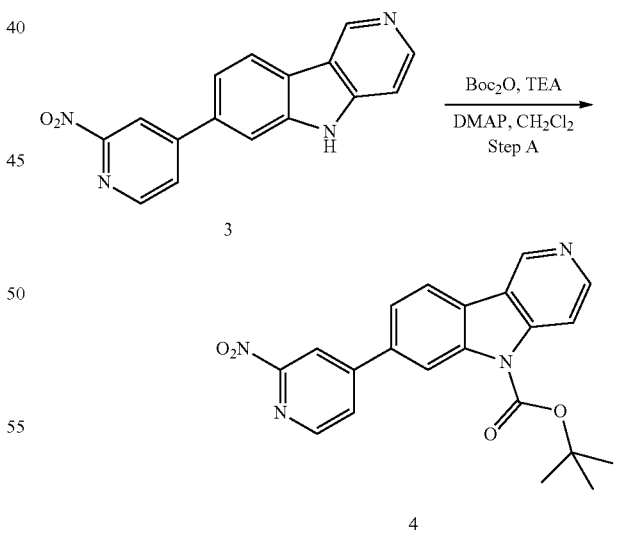

Step A

To a suspension of the title compound from Example 2 (0.020 g, 0.068 mmol) in dichloromethane (3 mL) was added triethylamine (0.3 mL, 2.16 mmol), di-tert-butyl dicarbonate (0.095 g, 0.408 mmol), and 4-(dimethylamino)-pyridine (0.0019 g, 0.0122 mmol). The reaction mixture was stirred at room temperature for 16 hours, diluted with ethyl acetate (50 mL) and water (20 mL). The organic phase was separated, dried over $Na_2SO_4$, filtered and the solvents removed in vacuo. The residue was purified on silica (12 g puriFlash, Interchim) using a Biotage Isolera One purification system employing an ethyl acetate/n-heptane gradient (5/95-→100/0-→100/0) to afford the title compound 4 as pale yellow solid (0.020 g, 75%).

$^1$H-NMR (400 MHz, $CDCl_3$) δ=9.38 (s, 1H), 8.83 (d, 1H), 8.76 (d, 1H), 8.73 (d, 1H), 8.63 (d, 1H), 8.26 (d, 1H), 8.17 (d, 1H), 8.03 (dd, 1H), 7.81 (dd, 1H), 1.84 (s, 9H)

MS (ESI); m/z=391.22 $[M+H]^+$;

Example 4

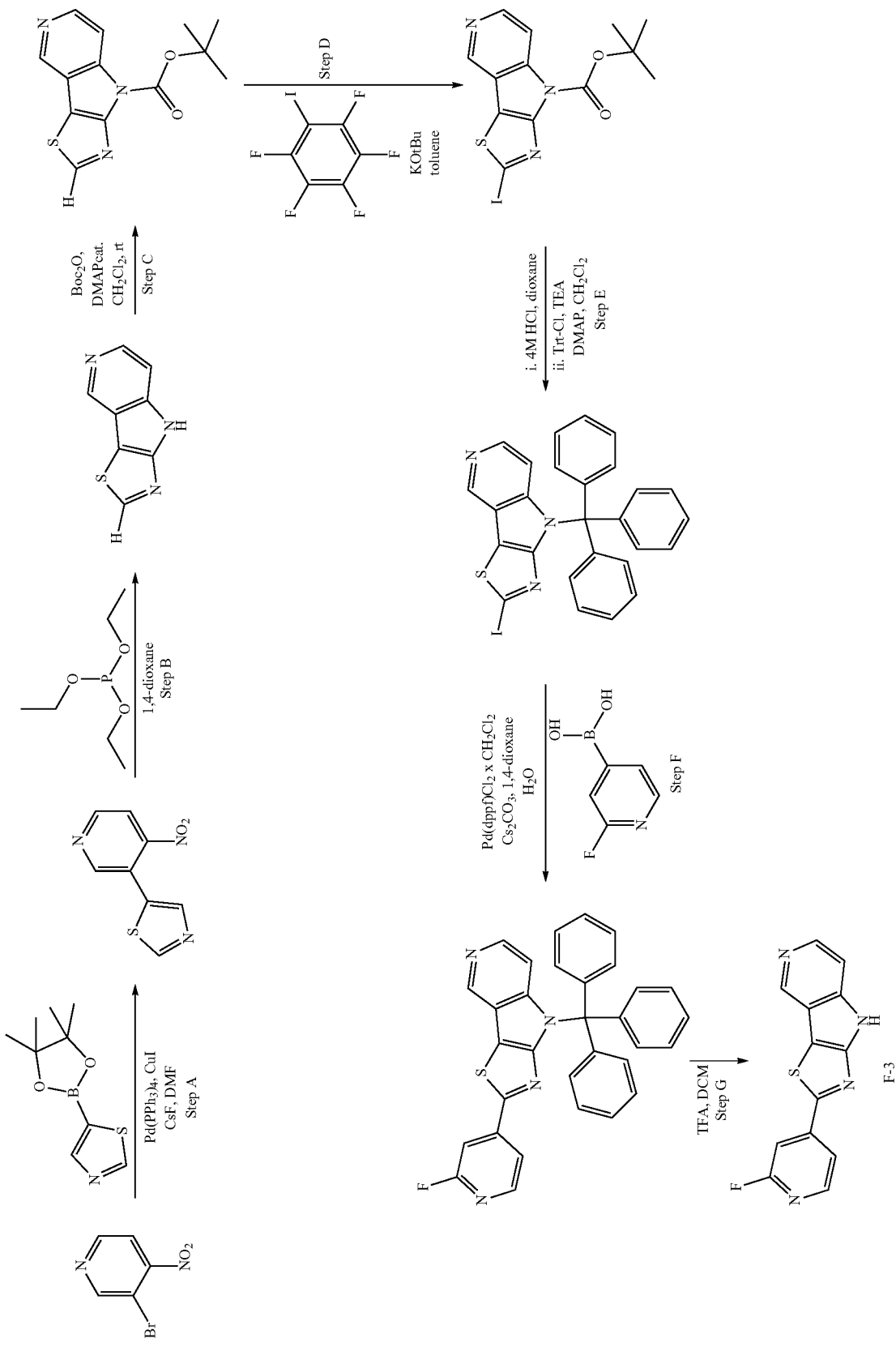

Step A

DMF (100 mL) was degased by vacuum/nitrogen filling cycles. 3-Bromo-4-nitropyridine (4.01 g, 19.74 mmol), 5-(4,4,5,5-tetramethyl-1,3,2-dioxaborolan-2-yl)thiazole (5 g, 23.69 mmol), cesium fluoride (7.50 g, 49.3 mmol), copper(I) iodide (0.376 g, 1.974 mmol) and Pd(Ph$_3$P)$_4$ (1.140 g, 0.987 mmol) were added and the crude was heated at 90° C. for 18 h. The reaction was cooled to room temperature and diluted with ethyl acetate. The organic phase was washed several times with water and brine, dried over Na$_2$SO$_4$, filtered and concentrated under reduced pressure. The residue was purified by chromatography on silica using a Biotage Isolera system employing dichloromethane/methanol (98/2) to afford the desired product (3.80 g, 93%).

$^1$H NMR (400 MHz, DMSO-d6) δ 9.32 (s, 1H), 9.02 (s, 1H), 8.96 (d, 1H), 8.16 (s, 1H), 8.08 (d, 1H).

Step B 4 batches of 0.75 g of 5-(4-nitropyridin-3-yl)thiazole in triethyl phosphite (20 ml, 117 mmol) were heated using a Biotage Initiator microwave at 120° C. for 15 min. Then, the reactions were poured into 200 ml of 6M HCl and stirred at room temperature for 3 h. The aqueous phase was cooled to 0° C., basiphied to pH 12 and extracted several times with dichloromethane containing 10% MeOH. The combined organic phases were dried over Na$_2$SO$_4$, filtered and concentrated under reduced pressure. The crude product was purified by chromatography on silica using a Biotage Isolera system employing a dichloromethane/methanol gradient (90/10 to 80/20). The solid was then triturated in ethyl acetate, filtered and dried to give the desired product (708.9 mg, 17%).

$^1$H NMR (400 MHz, DMSO-d6) δ 12.60 (s, 1H), 9.21 (s, 1H), 9.11 (s, 1H), 8.33 (d, 1H), 7.50 (d, 1H).

MS (ESI); m/z=176.15 [M+H]$^+$.

Step C

A suspension of 4H-thiazolo[5',4':4,5]pyrrolo[3,2-c]pyridine (709 mg, 4.05 mmol), BOC anhydride (1.879 ml, 8.09 mmol) and DMAP (dimethyl amino pyridine, 49.4 mg, 0.405 mmol) in dichloromethane (5 mL) was stirred at room temperature for 18 h. The crude product was concentrated under reduced pressure and purified by column chromatography on silica using a Biotage Isolera system employing a dichloromethane/methanol gradient (98/2 to 95/5) to give the desired compound (870 mg, 78%).

$^1$H NMR (400 MHz, DMSO-d6) δ 9.29 (s, 1H), 9.20 (s, 1H), 8.55 (d, 1H), 8.13 (d, 1H), 1.67 (s, 9H).

MS (ESI); m/z=276.16 [M+H]$^+$.

Step D

To a solution of tert-butyl 4H-thiazolo[5',4':4,5]pyrrolo[3,2-c]pyridine-4-carboxylate (1.0 g, 3.63 mmol) and 1,2,3,4,5-pentafluoro-6-iodobenzene (0.785 ml, 4.00 mmol) in toluene (50 mL) was added potassium tert-butoxide (0.204 g, 1.816 mmol). After 1 h at room temperature, the reaction was filtered and washed with toluene, water and dried to give the desired product (1.27 g, 87%).

$^1$H NMR (400 MHz, DMSO-d6) δ 9.19 (s, 1H), 8.55 (d, 1H), 8.09 (d, 1H), 1.67 (s, 9H).

MS (ESI); m/z=402.02 [M+H]+.

Step E

A solution of tert-butyl 2-iodo-4H-thiazolo[5',4':4,5]pyrrolo[3,2-c]pyridine-4-carboxylate (600 mg, 1.495 mmol) in 4N HCl in 1,4-dioxane (5 mL) and dichloromethane (10 mL) was stirred at room temperature for 18 h. The reaction was poured into 1N NaOH and the aqueous phase was adjusted to pH 12. Then, the aqueous phase was extracted with dichloromethane several times. The combined organics were dried over Na$_2$SO$_4$, filtered and concentrated under reduced pressure. The crude was suspended in dichloromethane (10 mL) and trityl-Cl (625 mg, 2.243 mmol), followed by the addition of DMAP (18.27 mg, 0.150 mmol) and triethylamine (0.208 ml, 1.495 mmol). After 18 h at room temperature, water was added and the aqueous phase was extracted several times with dichloromethane. The combined organic phases were dried over Na$_2$SO$_4$, filtered and evaporated under reduced pressure. The crude product was then purified by column chromatography on silica using a Biotage Isolera system employing a dichloromethane/methanol gradient (98/2) to afford the desired compound (180 mg) which contained a minor amount of by-products.

MS (ESI); m/z=543.68 [M+H]$^+$.

Step F 1,4-Dioxane (4 mL) and water (1 mL) were degassed by vacuum/nitrogen filling cycles. 2-Iodo-4-trityl-4H-thiazolo[5',4':4,5]pyrrolo[3,2-c]pyridine (80 mg, 0.147 mmol), (2-fluoropyridin-4-yl)boronic acid (31.1 mg, 0.221 mmol), Cs$_2$CO$_3$ (144 mg, 0.442 mmol) and PdCl$_2$(dppf)-dichloromethane adduct (12.02 mg, 0.015 mmol) were added and the reaction was heated at 120° C. for 6 h. Water was added and the reaction was extracted several times with dichloromethane. The combined organic phases were dried over Na$_2$SO$_4$, filtered and concentrated under reduced pressure. The residue was purified by column chromatography on silica using a Biotage Isolera system employing a dichloromethane/methanol gradient (98/2) to afford the desired product (30.5 mg, 40%).

$^1$H NMR (400 MHz, DMSO-d6) δ 9.20 (s, 1H), 8.31 (d, 1H), 8.09 (d, 1H), 7.51 (d, 1H), 7.47-7.29 (m, 15H), 7.19 (s, 1H), 6.59 (d, 1H).

MS (ESI); m/z=513.11 [M+H]$^+$.

Step G

To a solution of 2-(2-fluoropyridin-4-yl)-4-trityl-4H-thiazolo[5',4':4,5]pyrrolo[3,2-c]pyridine (28.0 mg, 0.055 mmol) in dichloromethane (4 mL) was added TFA (trifluoroacetic acid, 1 mL, 12.98 mmol). After 6 h at room temperature, the reaction was poured into 1N NaOH and the aqueous phase was extracted several times with dichloromethane. The combined organics were dried over Na$_2$SO$_4$, filtered and concentrated under reduced pressure. The crude was then purified by column chromatography on silica using a Biotage Isolera system employing a dichloromethane/methanol gradient (98/2 to 92/8) to afford the desired product F-3 (8.2 mg, 56%).

$^1$H NMR (400 MHz, DMSO-d6) δ 12.87 (s, 1H), 9.23 (s, 1H), 8.62-8.27 (m, 2H), 7.95 (d, 1H), 7.74 (s, 1H), 7.55 (d, 1H).

MS (ESI); m/z=271.08 [M+H]$^+$.

Example 5

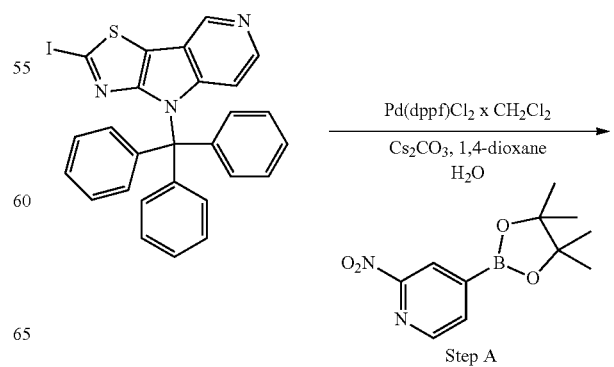

Step A

-continued

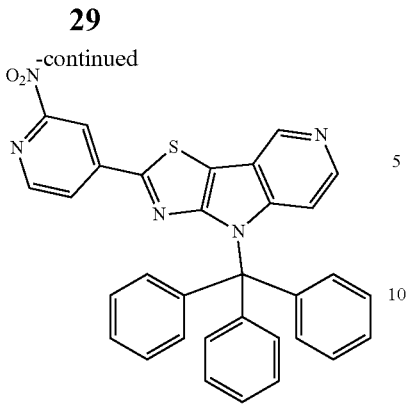
5

Step A 1,4-Dioxane (4 m) and water (1 mL) were degassed by vacuum/nitrogen filling cycles. 2-Iodo-4-trityl-4H-thiazolo[5',4':4,5]pyrrolo[3,2-c]pyridine (100 mg, 0.184 mmol), 2-nitro-4-(4,4,5,5-tetramethyl-1,3,2-dioxaborolan-2-yl)pyridine (69.0 mg, 0.276 mmol), 052003 (180 mg, 0.552 mmol) and $PdCl_2$(dppf)-dichloromethane adduct (15.03 mg, 0.018 mmol) were added and the reaction was heated at 120° C. for 6 h. Water was added and the reaction was extracted several times with dichloromethane. The combined organic phases were dried over $Na_2SO_4$, filtered and concentrated under reduced pressure. The crude product was then purified by column chromatography on silica using a Biotage Isolera system employing a dichloromethane/methanol gradient (98/2) to afford the desired product (28 mg, 28%).

$^1$H NMR (400 MHz, DMSO-d6) δ 9.24 (s, 1H), 8.72 (d, 1H), 8.17 (s, 1H), 8.14-8.05 (m, 2H), 7.47-7.31 (m, 15H), 6.66-6.57 (m, 1H).

MS (ESI); m/z=540.12 [M+H]$^+$.

Synthesis of $^{18}$F-Labeled Compounds

The n.c.a [$^{18}$F]fluoride (2-5 GBq) was trapped on a Sep-Pak Accell Plus QMA light cartridge (Waters) and eluted with a solution $K_2CO_3$/Kryptofix® 2.2.2. The water was removed using a stream of $N_2$ at 120° C. and co-evaporated to dryness with MeCN (3×1 mL). Afterwards, a solution of the dissolved precursor was added to the dried K[$^{18}$F]F-$K_{222}$ complex. The reaction vial was sealed and heated under conventional heating for 15 min at 130° C. Subsequently, the reaction mixture was quenched with water and the crude product was purified via semi-preparative HPLC. The isolated tracer was diluted with water (35 mL), trapped on a C-18 Plus cartridge (Waters), washed with water (5 mL), eluted with ethanol (1 mL) and formulated in saline.

Comparative Example $^{18}$F-1

$^{18}$F-1 (680 MBq) was synthesized according to the $^{18}$F-fluorination method described above using the corresponding nitro precursor molecule (M. Timothy et al., J. Labelled Comp. Radiopharm. (2013), 56(14), 736-740) (2.8 mg, 7.1 μmol) in dimethyl sulfoxide (0.6 mL). The radiochemical purity of 100% was determined by analytical reversed-phase HPLC ($t_R$(RAD-trace)=3.19 min). The identity of $^{18}$F-1 was confirmed by comparing the retention time with the non-radioactive reference F-1.

Example $^{18}$F-2

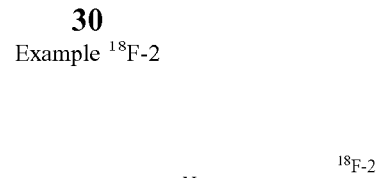

$^{18}$F-2 (418 MBq) was synthesized according to the $^{18}$F-fluorination method described above using precursor molecule compound 4 (2.4 mg) which was obtained in Example 3 above in dimethyl sulfoxide (0.6 mL). The radiochemical purity of 98% was determined by analytical reversed-phase HPLC ($t_R$(RAD-trace)=3.8 min). The identity of $^{18}$F-2 was confirmed by comparing the retention time with the non-radioactive reference F-2.

Example $^{18}$F-3

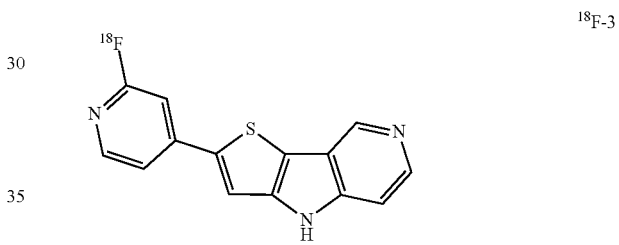

$^{18}$F-3 was synthesized according to the $^{18}$F-fluorination method described above using precursor molecule compound 5 which was obtained in Example 5 above in dimethyl sulfoxide. Before preparative HPLC, the trityl protecting group was cleaved by addition of 1N sulfuric acid and heating at 120° C. The radiochemical purity was determined by analytical reversed-phase HPLC. The identity of $^{18}$F-3 was confirmed by comparing the retention time with the non-radioactive reference F-3.

Determination of Binding in AD and Healthy Control Brain Homogenates

20 μg of human Alzheimer disease brain homogenate was incubated with a dilution series of each test compound (1000 to 0.06 nM) in the presence of 800 Bq of $^{18}$F-labeled Tau binder. The samples were shaken at 110 rpm for 45 min at 37° C. Samples were then filtered through GF/B 96 well filter plates and washed twice with 300 μL assay buffer (PBS containing 0.1% BSA and 2% DMSO). Thereafter, filter plates were sealed and a Fuji Film Imaging Plate (BAS-SR2025) was placed on top. The imaging plate was analyzed after overnight exposition using a Fuji Film BAS-5000. Non-specific signal was determined with samples containing $^{18}$F-labeled Tau-reference binder in the presence of assay buffer without brain substrate and competitor. Specific binding was calculated by subtracting the non-specific signal from the measured samples signal. The unblocked $^{18}$F-labeled Tau-binder signal was defined as total binding. IC50 values were calculated by Prism V7 (GraphPad) setting total binding to 100%.

Results:

High tau-affinity of compounds F-1 and F-2 were found in a competition assay using human AD brain homogenate. IC50 values for tau binding of <2 nM were measured for both compounds. For compound F-3 good affinity towards tau was found in the same assay.

Determination of the Binding Affinity to K18 Tau Aggregates 200 ng of aggregated recombinant human K18 fibrils were incubated with a dilution series of each test compound (1000 to 0.06 nM) in the presence of 3 nM of $^3$H-labeled Tau binder. The samples were shaken at 110 rpm for 60 min at 37° C. Samples were then filtered through GF/B 96 well filter plates and washed twice with 200 μL assay buffer (PBS containing 0.1% BSA and 2% DMSO). Thereafter, 40 μL of MicroScint 40 was added to each well of the filter plate. Filter plates were sealed and then placed shaking at 110 rpm at 37° C. for 15 min. Measurement was done by TopCount NXT HTS (PerkinElmer). Non-specific signal was determined with samples containing $^3$H-labeled Tau binder in the presence of 2.5 μM unlabeled Tau-reference binder and K18 fibrils. Specific binding was calculated by subtracting the non-specific signal from the measured samples signal. The unblocked $^3$H-labeled Tau-binder signal was defined as total binding. IC50 values were calculated by Prism V7 (GraphPad) setting total binding to 100%.

Determination of the Binding Affinity to Amyloid-Beta in AD Brain Homogenate

20 μg of human Alzheimer disease brain homogenate was incubated with a dilution series of each test compound (1000 to 0.06 nM) in the presence of 700 Bq of $^3$H-labeled beta-amyloid binder PIB. The samples were shaken at 110 rpm for 60 min at 37° C. Samples were then filtered through GF/B 96 well filter plates and washed twice with 200 μL assay buffer (PBS containing 0.1% BSA and 2% DMSO). Thereafter, 40 μL Szintillation cocktail was added and the filter plates were sealed. The counts were then counted using a TopCount (Perkin Elmer). Non-specific signal was determined with samples containing $^3$H-labeled beta-amyloid binder in the presence of assay buffer without brain substrate and competitor. Specific binding was calculated by subtracting the non-specific signal from the measured samples signal. The unblocked $^3$H-labeled beta-amyloid binder signal was defined as total binding. IC50 values were calculated by Prism V7 (GraphPad) setting total binding to 100%.

Results:

Low affinity of compounds F-1 and F-2 for beta-amyloid was found in a competition assay using human AD brain homogenate. $IC_{50}$ values for beta-amyloid binding of >1 μM were measured for all compounds.

Determination of the Binding Affinity to MAO-A in HC Brain Homogenate

20 μg of mouse whole brain or human brain homogenate (without AD pathology, HC) was incubated with a dilution series of each test compound (1000 to 0.06 nM) in the presence of 700 Bq of $^3$H-labeled MAO-A binder Harmine. The samples were shaken at 110 rpm for 60 min at 37° C. Samples were then filtered through GF/B 96 well filter plates and washed twice with 200 μL assay buffer (PBS containing 0.1% BSA and 2% DMSO). Thereafter, 40 μL Szintillation cocktail was added and the filter plates were sealed. The counts were then counted using a TopCount (Perkin Elmer). Non-specific signal was determined with samples containing $^3$H-Harmine in the presence of assay buffer without brain substrate and competitor. Specific binding was calculated by subtracting the non-specific signal from the measured samples signal. The unblocked $^3$H-Harmine signal was defined as total binding. IC50 values were calculated by Prism V7 (GraphPad) setting total binding to 100%.

Results:

In the mouse brain homogenate, compound F-1 showed a high off-target affinity towards MAO-A of 4.6 nM in the $^3$H-Harmine competition assay. The affinity of compound F-2 was reduced to 51.4 nM. Low affinity MAO-A binding was found for compound F-3 in the same assay.

Using the human control brain homogenate, compound F-1 showed a high off-target affinity towards MAO-A of 5.9 nM in the $^3$H-Harmine competition assay. The affinity of compound F-2 was reduced to 37.2 nM.

Determination of the Binding Affinity to MAO-B in HC Brain Homogenate

20 μg of human brain homogenate (without AD pathology) was incubated with a dilution series of each test compound (1000 to 0.06 nM) in the presence of 700 Bq of $^3$H-labeled MAO-B binder Deprenyl. The samples were shaken at 110 rpm for 60 min at 37° C. Samples were then filtered through GF/B 96 well filter plates and washed twice with 200 μL assay buffer (PBS containing 0.1% BSA and 2% DMSO). Thereafter, 40 μL Szintillation cocktail was added and the filter plates were sealed. The counts were then counted using a TopCount (Perkin Elmer). Non-specific signal was determined with samples containing $^3$H-deprenyl in the presence of assay buffer without brain substrate and competitor. Specific binding was calculated by subtracting the non-specific signal from the measured samples signal. The unblocked $^3$H-deprenyl signal was defined as total binding. $IC_{50}$ values were calculated by Prism V7 (GraphPad) setting total binding to 100%.

Results:

In the human HC brain homogenate, compound F-1 showed a high off-target affinity towards MAO-B of 78 nM in the $^3$H-deprenyl competition assay. The affinity of compound F-2 was reduced to 778 nM.

TABLE 1

Summary of pre-clinical characteristics

| Criteria for Tau-PET-Imaging agents | Compound $^{18}$F-1 | Compound $^{18}$F-2 | Compound $^{18}$F-3 |
|---|---|---|---|
| High affinity to Tau ($IC_{50}$ in AD brain homogenate)[b] | +++ (<2 nM)[a] | +++ (<2 nM)[a] | + (13.4 nM)[a] |
| High affinity to Tau ($IC_{50}$ using K18 Tau aggregates)[b] | + (19.6 nM)[a] | ++ (3 nM)[a] | n.d. |
| Low affinity to amyloid-beta ($IC_{50}$ in AD brain homogenate)[b] | +++[a] >1 μM | +++[a] >1 μM | n.d. |
| Low affinity to MAO A ($IC_{50}$ in mouse brain homogenate)[b] | − (4.6 nM)[a] | ○ (51.4 nM)[a] | +++ (>1000 nM)[a] |
| Low affinity to MAO A | − | ○ | n.d. |

TABLE 1-continued

Summary of pre-clinical characteristics

| Criteria for Tau-PET-Imaging agents | Compound $^{18}$F-1 | Compound $^{18}$F-2 | Compound $^{18}$F-3 |
|---|---|---|---|
| (IC$_{50}$ in human HC brain homogenate)[b] | (5.9 nM)[a] | (37.2 nM)[a] | |
| Low affinity to MAO B | o | ++ | n.d. |
| (IC$_{50}$ in human HC brain homogenate)[b] | (78 nM) | (778 nM) | |
| Signal to noise | – | o | n.d. |
| (% signal intensity in HC brain homogenate compared to tracer signal in AD brain homogenate)[a],[c] | (85%) | (66%) | |
| High signal to noise | – | + | n.d. |
| (% signal intensity in mouse brain homogenate compared to tracer signal in AD brain homogenate)[a],[c] | (93%) | (57%) | |

– poor,
o moderate,
+ good,
++ very good,
+++ excellent,
n.d.: not determined
[a] see experimental section above, values for both compounds obtained in the same assay
[b] determined with the non-radioactive fluorine-19 derivatives F-1 and F-2;
[c] determined with the radioactive fluorine-18 derivatives $^{18}$F-1 and $^{18}$F-2;

As can be seen from Table 1, the prior art compound $^{18}$F-1 has limitations especially in respect to:
- Affinity for MAO A and MAO B and thus low selectivity to Tau,
- Not having low signal in healthy brain,
- Reduced affinity to K18 Tau aggregates On the other hand, compound $^{18}$F-2 shows:
- Less affinity to MAO A in whole mouse brain homogenate (11-fold higher IC$_{50}$ than compound $^{18}$F-1),
- Less affinity to MAO A in human control brain homogenate (6.3-fold higher IC$_{50}$ than compound $^{18}$F-1),
- Less affinity to MAO B in HC brain homogenate (>10-fold higher IC$_{50}$ than compound $^{18}$F-1),
- Higher signal to noise ratio, determined by the binding in AD brain homogenate and HC brain homogenate (19% less relative signal in HC brain homogenate ratio than $^{18}$F-1),
- Similar affinity to AD brain homogenate and K18 Tau aggregates.

On the other hand, compound $^{18}$F-3 shows:
- Less affinity to MAO A in whole mouse brain homogenate (>100-fold higher IC$_{50}$) than compound $^{18}$F-1, Due at least to its high affinity to Tau in AD brain homogenate and K18 aggregates, and lower binding affinity to other brain targets, compound $^{18}$F-2 has significantly better properties for determining and quantifying Tau deposits in the brain by positron emission tomography than the prior art compound $^{18}$F-1.

The invention claimed is:

1. A compound of the formula (II)

(II)

as well as pharmaceutically acceptable salts, hydrates, solvates, prodrugs and polymorphs thereof;
wherein R$^1$ is selected from the group consisting of $^{18}$F, F and LG;
R$^2$ is H or PG;
PG is a protecting group;
LG is a leaving group,
wherein the hydrogen in formula II are independently selected from $^1$H, $^2$H and $^3$H.

2. The compound according to claim 1, which is

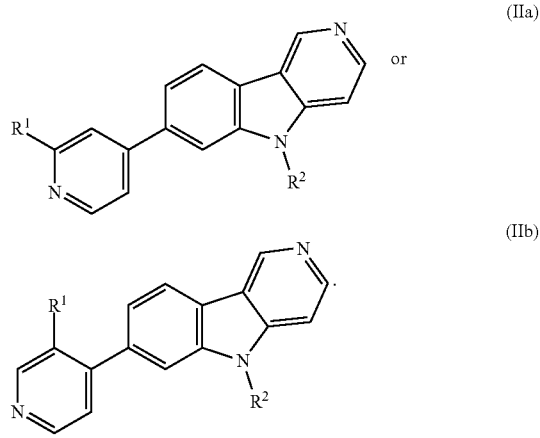

3. A compound of the formula (III)

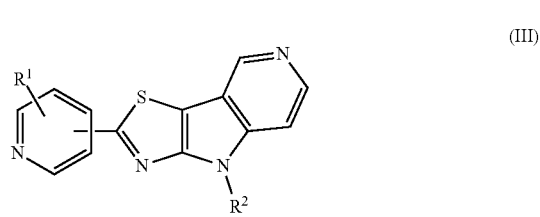

as well as pharmaceutically acceptable salts, hydrates, solvates, prodrugs and polymorphs thereof;
wherein
$R^1$ is selected from the group consisting of $^{18}F$, F and LG;
$R^2$ is H or PG;
PG is a protecting group;
LG is a leaving group,
wherein the hydrogen in the formula III are independently selected from $^1H$, $^2H$ and $^3H$.

4. The compound according to claim 3, which is

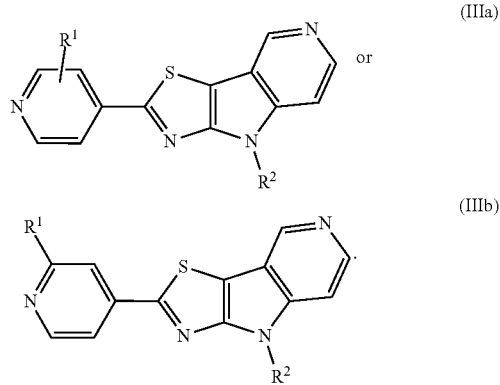

5. The compound according to claim 1, wherein $R^1$ is $^{18}F$ and $R^2$ is H, $R^1$ is F and $R^2$ is H, or $R^1$ is LG and $R^2$ is H or PG.

6. The compound according to claim 1, wherein LG is nitro, halogen or trimethyl ammonium.

7. The compound according to claim 1, wherein PG is tert-butyloxycarbonyl (BOC), triphenylmethyl (Trityl) or dimethoxytrityl (DMT).

8. The compound according to claim 1, wherein $R^1$ is $^{18}F$ and/or the compound contains at least one $^3H$.

9. A diagnostic composition comprising a compound as defined in claim 8 and optionally a pharmaceutically acceptable carrier, diluent, adjuvant or excipient.

10. A method of imaging Tau aggregates by positron emission tomography, comprising administering a diagnostically effective amount of a compound as defined in claim 8 to a patient and imaging Tau aggregates in the patient.

11. A method of diagnosing a disorder associated with Tau aggregates or a tauopathy by positron emission tomography, comprising administering a diagnostically effective amount of a compound as defined in claim 8 to a patient and imaging Tau aggregates in the patient.

12. The method according to claim 11, wherein the disorder is selected from Alzheimer's disease (AD), familial AD, Creutzfeldt-Jacob disease, dementia pugilistica, Down's Syndrome, Gerstmann-Sträussler-Scheinker disease, inclusion-body myositis, prion protein cerebral amyloid angiopathy, traumatic brain injury, amyotrophic lateral sclerosis, Parkinsonism-dementia complex of Guam, non-Guamanian motor neuron disease with neurofibrillary tangles, argyrophilic grain disease, corticobasal degeneration (CBD), diffuse neurofibrillary tangles with calcification, frontotemporal dementia with Parkinsonism linked to chromosome 17, Hallervorden-Spatz disease, multiple system atrophy, Niemann-Pick disease type C, pallido-ponto-nigral degeneration, Pick's disease (PiD), progressive subcortical gliosis, progressive supranuclear palsy (PSP), subacute sclerosing panencephalitis, tangle only dementia, postencephalitic Parkinsonism, myotonic dystrophy, Tau panencephalopathy, AD-like with astrocytes, GSS with Tau, mutations in LRRK2, chronic traumatic encephalopathy, familial British dementia, familial Danish dementia, frontotemporal lobar degeneration, Guadeloupean Parkinsonism, neurodegeneration with brain iron accumulation, SLC9A6-related mental retardation, white matter tauopathy with globular glial inclusions, traumatic stress syndrome, epilepsy, Lewy body dementia (LBD), hereditary cerebral hemorrhage with amyloidosis of the Dutch type, mild cognitive impairment (MCI), multiple sclerosis, Parkinson's disease, atypical parkinsonism, HIV-related dementia, adult onset diabetes, senile cardiac amyloidosis, endocrine tumors, glaucoma, ocular amyloidosis, primary retinal degeneration, macular degeneration, optic nerve drusen, optic neuropathy, optic neuritis, lattice dystrophy, Huntington's disease, ischemic stroke and psychosis in AD.

13. An in vitro screening tool, which comprises a compound according to claim 5 wherein $R^1$ is F and $R^2$ is H.

14. A method of preparing a compound as defined in claim 5 wherein $R^1$ is $^{18}F$ and $R^2$ is H, the method comprising reacting a compound as defined in claim 5 wherein $R^1$ is LG and $R^2$ is H or PG with a [$^{18}F$]fluorinating agent, wherein the method further comprises cleaving of the protecting group PG, if present.

15. A kit for preparing a radiopharmaceutical preparation, said kit comprising a sealed vial containing a predetermined quantity of a compound as defined in claim 5, wherein $R^1$ is LG and $R^2$ is H or PG.

16. A method of collecting data for the diagnosis of a disorder associated with tau aggregates in a sample or a patient comprising:
(a) bringing a sample or a specific body part or body area suspected to contain a tau aggregate into contact with a compound as defined in claim 8;
(b) allowing the compound to bind to the tau aggregate;
(c) detecting the compound bound to the tau aggregate; and
(d) optionally correlating the presence or absence of compound binding with the tau aggregate with the presence or absence of tau aggregate in the sample or specific body part or body area.

17. A method which comprises the steps of:
(a) bringing a sample or a specific body part or body area suspected to contain a tau aggregate into contact with the compound as defined in claim 8, which compound specifically binds to the tau aggregate;
(b) allowing the compound to bind to the tau aggregate to form a compound/tau aggregate complex;
(c) detecting the formation of the compound/tau aggregate complex;
(d) optionally correlating the presence or absence of the compound/tau aggregate complex with the presence or absence of tau aggregate in the sample or specific body part or body area; and
(e) optionally comparing the amount of the compound/tau aggregate to a normal control value
wherein the method is
a method of collecting data for determining a predisposition to a disorder associated with tau aggregates in a patient comprising detecting the specific binding of a compound as defined in claim 8 to a tau aggregate in a sample or in situ, or
a method of collecting data for predicting responsiveness of a patient suffering from a disorder associated with tau aggregates and being treated with a medicament.

18. The compound according to claim 3, wherein $R^1$ is $^{18}F$ and/or the compound contains at least one $^3H$.

19. The compound according to claim 18, wherein $R^1$ is $^{18}F$.

20. A diagnostic composition comprising a compound as defined in claim 18 and optionally a pharmaceutically acceptable carrier, diluent, adjuvant or excipient.

21. A method of imaging Tau aggregates, which comprises administering a diagnostically effective amount of a compound as defined in claim 18 to a patient and the imaging the Tau aggregates in the patient.

22. A method of diagnosing a disorder associated with Tau aggregates or a tauopathy, which comprises administering a diagnostically effective amount of a compound as defined in claim 18 to a patient and imaging the Tau aggregates in the patient.

23. The method according to claim 22, wherein the disorder is selected from Alzheimer's disease (AD), familial AD, Creutzfeldt-Jacob disease, dementia pugilistica, Down's Syndrome, Gerstmann-Sträussler-Scheinker disease, inclusion-body myositis, prion protein cerebral amyloid angiopathy, traumatic brain injury, amyotrophic lateral sclerosis, Parkinsonism-dementia complex of Guam, non-Guamanian motor neuron disease with neurofibrillary tangles, argyrophilic grain disease, corticobasal degeneration (CBD), diffuse neurofibrillary tangles with calcification, frontotemporal dementia with Parkinsonism linked to chromosome 17, Hallervorden-Spatz disease, multiple system atrophy, Niemann-Pick disease type C, pallido-ponto-nigral degeneration, Pick's disease (PiD), progressive subcortical gliosis, progressive supranuclear palsy (PSP), subacute sclerosing panencephalitis, tangle only dementia, postencephalitic Parkinsonism, myotonic dystrophy, Tau panencephalopathy, AD-like with astrocytes, GSS with Tau, mutations in LRRK2, chronic traumatic encephalopathy, familial British dementia, familial Danish dementia, frontotemporal lobar degeneration, Guadeloupean Parkinsonism, neurodegeneration with brain iron accumulation, SLC9A6-related mental retardation, white matter tauopathy with globular glial inclusions, traumatic stress syndrome, epilepsy, Lewy body dementia (LBD), hereditary cerebral hemorrhage with amyloidosis of the Dutch type, mild cognitive impairment (MCI), multiple sclerosis, Parkinson's disease, atypical parkinsonism, HIV-related dementia, adult onset diabetes, senile cardiac amyloidosis, endocrine tumors, glaucoma, ocular amyloidosis, primary retinal degeneration, macular degeneration, optic nerve drusen, optic neuropathy, optic neuritis, lattice dystrophy, Huntington's disease, ischemic stroke and psychosis in AD.

24. The method according to claim 23, wherein the disorder is Alzheimer's disease (AD).

25. An in vitro screening tool, which comprises a compound according to claim 3 wherein $R^1$ is F and $R^2$ is H.

26. A method of preparing a compound as defined in claim 3 wherein $R^1$ is $^{18}F$ and $R^2$ is H, the method comprising reacting a compound as defined in claim 4 wherein $R^1$ is LG and $R^2$ is H or PG with a $[^{18}F]$fluorinating agent, wherein the method further comprises cleaving of the protecting group PG, if present.

27. A kit for preparing a radiopharmaceutical preparation, said kit comprising a sealed vial containing a predetermined quantity of a compound as defined in claim 3, wherein $R^1$ is LG and $R^2$ is H or PG.

28. A method of collecting data for the diagnosis of a disorder associated with tau aggregates in a sample or a patient comprising:
 (a) bringing a sample or a specific body part or body area suspected to contain a tau aggregate into contact with a compound as defined in claim 18;
 (b) allowing the compound to bind to the tau aggregate;
 (c) detecting the compound bound to the tau aggregate; and
 (d) optionally correlating the presence or absence of compound binding with the tau aggregate with the presence or absence of tau aggregate in the sample or specific body part or body area.

29. A method which comprises the steps of:
 (a) bringing a sample or a specific body part or body area suspected to contain a tau aggregate into contact with the compound as defined in claim 18, which compound specifically binds to the tau aggregate;
 (b) allowing the compound to bind to the tau aggregate to form a compound/tau aggregate complex;
 (c) detecting the formation of the compound/tau aggregate complex;
 (d) optionally correlating the presence or absence of the compound/tau aggregate complex with the presence or absence of tau aggregate in the sample or specific body part or body area; and
 (e) optionally comparing the amount of the compound/tau aggregate to a normal control value
 wherein the method is
 a method of collecting data for determining a predisposition to a disorder associated with tau aggregates in a patient comprising detecting the specific binding of a compound as defined in claim 18 to a tau aggregate in a sample or in situ, or
 a method of collecting data for predicting responsiveness of a patient suffering from a disorder associated with tau aggregates and being treated with a medicament.

30. The compound according to claim 8, wherein $R^1$ is $^{18}F$.

31. The method according to claim 12, wherein the disorder is Alzheimer's disease (AD).

* * * * *